(12) United States Patent
Castro Pineiro et al.

(10) Patent No.: US 6,906,085 B2
(45) Date of Patent: Jun. 14, 2005

(54) TETRAHYDROPYRAN DERIVATIVES AS NEUROKININ RECEPTOR ANTAGONISTS

(75) Inventors: Jose Luis Castro Pineiro, Bishops Stortford (GB); Piotr Antoni Raubo, Bishops Stortford (GB); Christopher John Swain, Duxford (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/466,700

(22) PCT Filed: Jan. 16, 2002

(86) PCT No.: PCT/GB02/00179

§ 371 (c)(1),
(2), (4) Date: Jul. 15, 2003

(87) PCT Pub. No.: WO02/057250

PCT Pub. Date: Jul. 25, 2002

(65) Prior Publication Data

US 2004/0063974 A1 Apr. 1, 2004

(30) Foreign Application Priority Data

Jan. 17, 2001 (GB) .............................................. 0101246
Sep. 10, 2001 (GB) .............................................. 0121876

(51) Int. Cl.$^7$ ..................... A61K 31/35; A61K 31/445; C07D 309/10; C07D 401/04; C07D 401/06
(52) U.S. Cl. ....................... 514/326; 514/382; 514/383; 514/384; 514/459; 514/460; 546/207; 549/416; 549/419; 548/252; 548/263.2; 548/268.8
(58) Field of Search .................. 546/207; 548/252, 548/263.2, 268.8; 514/382, 383, 384, 460, 459; 549/416, 419, 423

(56) References Cited

FOREIGN PATENT DOCUMENTS

WO          WO 0056727 A          9/2000

OTHER PUBLICATIONS

Chemical Abstracts Service, vol. 70, No. 25, Jun. 23, 1969, Y. Kai, M. Shimizu: "Phenolic constituents from *Cryptomeria joaponica* wood, V. Structure of hydroxysugiresinol" vol. 14, No. 8, 1986, pp. 430–433.

*Primary Examiner*—Bernard Dentz
(74) *Attorney, Agent, or Firm*—J. Eric Thies; Melvin Winokur

(57) ABSTRACT

The present invention relates compounds of the formula (I):

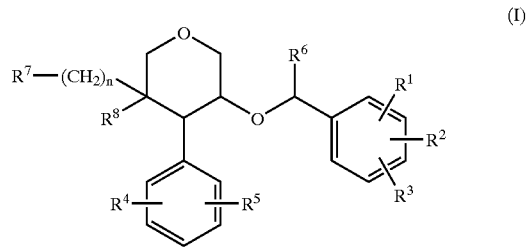

wherein $R^1$, $R^2$, $R^3$, $R^4$, $R^5$, $R^6$, $R^7$ and $R^8$ represent a variety of substituents; and pharmaceutically acceptable salts thereof. The compounds are of particular use in the treatment or prevention of depression, anxiety, pain, inflammation, migraine, emesis or postherpetic neuralgia.

14 Claims, No Drawings

TETRAHYDROPYRAN DERIVATIVES AS NEUROKININ RECEPTOR ANTAGONISTS

CROSS REFERENCE TO RELATED APPLICATIONS

This application is a U.S. National Phase application under 35 U.S.C. §371 of PCT Application No. PCT/GB02/00179, filed Jan. 16, 2002, which claims priority under 35 U.S.C. §119 from GB Application No. 0101246.7, filed Jan. 17, 2001, and GB Application No. 0121876.7, filed Sep. 10, 2001.

This invention relates to a class of tetrahydropyran compounds which are useful as tachykinin antagonists. More particularly, the compounds of the invention are useful as neurokinin 1 (NK-1) receptor antagonists.

The present invention provides compounds of the formula (I):

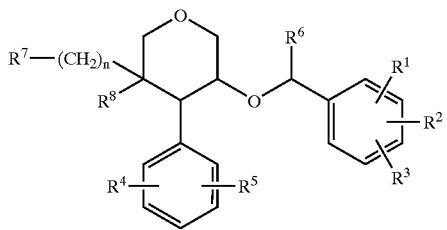

wherein $R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ is hydrogen, halogen, $C_{1-6}$alkyl, $C_{1-6}$alkoxy, fluoro$C_{1-6}$alkyl, fluoro$C_{1-6}$alkoxy, hydroxy, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, fluoro$C_{1-6}$alkyl or $C_{1-6}$alkoxy substituted by $C_{1-4}$alkoxy;

$R^6$ represents hydrogen or a $C_{1-4}$alkyl group optionally substituted by a hydroxy group;

$R^7$ represents halogen, hydroxy, $C_{2-4}$alkenyl, $C_{2-4}$alkynyl, $C_{1-6}$alkoxy, $N_3$, $-NR^9R^{10}$, $-NR^aCOR^b$, $-OSO_2R^a$, $-(CH_2)_pNR^a(CH_2)_qCOOR^b$, $COR^a$, $COOR^a$, $-N=C=O$, a 5- or 6-membered cyclic ether which is optionally substituted at any substitutable position by one or two substituents selected from $=O$, $=S$, halogen, hydroxy, $C_{1-4}$alkyl, $C_{1-4}$alkoxy, fluoro$C_{1-4}$alkyl fluoro$C_{1-4}$alkoxy, $COR^e$ and $CO_2R^e$, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from $=O$, $=S$, halogen, hydroxy, $-SH$, $COR^a$, $CO_2R^a$, $-ZNR^9R^{10}$, $C_{1-4}$alkyl, hydroxy$C_{1-4}$alkyl, fluoro$C_{1-4}$alkyl, chloro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group, and wherein said $C_{2-4}$alkenyl and $C_{2-4}$alkynyl groups are optionally substituted by a substituent selected from halogen, hydroxy, $N_3$, $-NR^9R^{10}$, $-NR^aCOR^b$, $-OSO_2R^a$, $-(CH_2)_pNR^a(CH_2)_q$ $COOR^b$, $COR^a$ or $COOR^a$, and where $R^e$ is hydrogen, $C_{1-4}$alkyl or benzyl;

or $R^7$ represents a C-linked nitrogen-containing ring of the formula

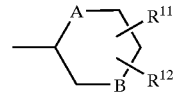

wherein A represents $NR^{13}$ or O, and

B represents a bond, $CH_2$, $NR^{13}$ or O, wherein one or both hydrogen atoms in said $CH_2$ moiety may be replaced with one or both of $R^{11}$ and $R^{12}$, or alternatively, one of the hydrogen atoms in said $CH_2$ moiety together with a hydrogen atom from an adjacent carbon are replaced by a double bond;

with the proviso that when A is O, then B is $NR^{13}$;

and with the further proviso that when $R^7$ represents said C-linked nitrogen-containing ring, n is zero and $R^8$ is hydrogen;

$R^8$ represents hydrogen, $C_{1-6}$alkyl, fluoro$C_{1-6}$alkyl, hydroxy, $C_{1-6}$alkoxy or hydroxy$C_{1-6}$alkyl;

$R^9$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group, or $R^9$ is a five membered or six membered nitrogen-containing heteroaromatic ring as previously defined;

$R^{10}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

or $R^9$, $R^{10}$ and the nitrogen atom to which they are attached form a heteroaliphatic ring of 4 to 7 ring atoms, optionally substituted by one or two groups selected from hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, or a five membered or six membered nitrogen-containing heteroaromatic ring as previously defined, or said heteroaliphatic ring is substituted by a spiro-fused lactone ring, and said heteroaliphatic ring optionally containing a double bond, which heteroaliphatic ring may optionally contain an oxygen or sulphur ring atom, a group $S(O)$ or $S(O)_2$ or a second nitrogen atom which will be part of a NH or $NR^d$ moiety, where $R^d$ is $C_{1-4}$alkyl optionally substituted by hydroxy or $C_{1-4}$alkoxy;

or $R^9$, $R^{10}$ and the nitrogen atom to which they are attached form a non-aromatic azabicyclic ring system of 6 to 12 ring atoms;

or $R^9$, $R^{10}$ and the nitrogen atom to which they are attached form a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S;

$R^{11}$ and $R^{12}$ each independently represent hydrogen, hydroxy, $COR^e$, $CO_2R^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group;

or, when they are attached to the same carbon atom, $R^{11}$ and $R^{12}$ may together represent $=O$, $=CHCO_2R^a$, $-O(CH_2)_mO-$, $-CH_2O(CH_2)_k-$, $-CH_2OCH_2C(O)-$, $-CH_2OCH_2CH(OH)-$, $-CH_2OCH_2C(CH_3)_2-$, $-CH_2OC(CH_3)_2CH_2-$, $-C(CH_3)_2OCH_2CH_2-$, $-CH_2C(O)OCH_2-$, $-OC(O)CH_2CH_2-$, $-C(O)OCH_2CH_2-$, $-C(O)OC(CH_3)_2CH_2-$, $-C(O)OCH_2C(CH_3)_2-$, —OCH$_2$(CH$_2$)$_k$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

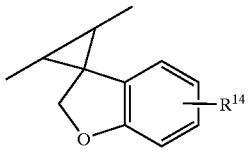

or, where they are attached to adjacent carbon atoms, R$^{11}$ and R$^{12}$ may together represent —OCH$_2$CH$_2$— or —OCH$_2$CH(OH)—, or R$^{11}$ and R$^{12}$ may together form a fused benzene ring;

or, R$^{11}$ and R$^{12}$ together form a C$_{1-2}$alkylene bridge across the pyrrolidine, piperidine, morpholine or piperazine ring to which they are attached;

R$^{13}$ represents hydrogen, benzyl, C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

R$^{14}$ represents hydrogen, halogen, hydroxy, C$_{1-4}$alkyl, hydroxyC$_{1-4}$alkyl or fluoroC$_{1-4}$alkyl;

Z represents a bond, C$_{1-6}$alkylene or C$_{3-6}$cycloalkylene;

k is 1, 2 or 3;
m is 1 or 2;
n is zero, 1 or 2;
p is 1 or 2; and
q is 1 or 2;
and pharmaceutically acceptable salts thereof.

A preferred class of compounds of formula (I) is that wherein R$^1$ is hydrogen, C$_{1-4}$alkyl, C$_{1-4}$alkoxy, halogen or CF$_3$.

Another preferred class of compounds of formula (I) is that wherein R$^2$ is hydrogen, C$_{1-4}$alkyl, C$_{1-4}$alkoxy, halogen or CF$_3$.

Also preferred is the class of compounds of formula (I) wherein R$^3$ is hydrogen, fluorine, chlorine or CF$_3$.

A particularly preferred class of compounds of formula (I) is that wherein R$^1$ is fluorine, chlorine or CF$_3$.

Another particularly preferred class of compounds of formula (I) is that wherein R$^2$ is hydrogen, fluorine, chlorine or CF$_3$.

Also particularly preferred is the class of compounds of formula (I) wherein R$^3$ is hydrogen, fluorine, chlorine or CF$_3$.

Preferably R$^1$ and R$^2$ are in the 3 and 5 positions of the phenyl ring.

More preferably R$^1$ is 3-fluoro or 3-CF$_3$.
More preferably R$^2$ is 5-fluoro or 5-CF$_3$.
More preferably R$^3$ is hydrogen.
Most preferably R$^1$ is 3-F or 3-CF$_3$, R$^2$ is 5-CF$_3$ and R$^3$ is hydrogen.

A further preferred class of compound of formula (I) is that wherein R$^4$ is hydrogen or fluorine, especially hydrogen.

Another preferred class of compounds of formula (I) is that wherein R$^5$ is hydrogen, fluorine, chlorine or CF$_3$.

Preferably R$^4$ is hydrogen or 3-fluoro, especially hydrogen, and R$^6$ is hydrogen or 4-fluoro.

R$^6$ is preferably C$_{1-4}$-alkyl optionally substituted by hydroxy. In particular, R$^6$ is preferably a methyl or hydroxymethyl group. Most especially, R$^6$ is a methyl group.

Where —NR$^9$R$^{10}$ is defined as a substituent R$^7$ or as a substituent on a heteroaromatic ring in the definition of R$^7$, then R$^9$ may aptly be a C$_{1-4}$alkyl group or a C$_{2-4}$alkyl group substituted by a hydroxyl or C$_{1-2}$alkoxy group, R$^{10}$ may aptly be a C$_{1-4}$alkyl group or a C$_{2-4}$alkyl group substituted by a hydroxyl or C$_{1-2}$alkoxy group, or R$^9$ and R$^{10}$ may be linked so that, together with the nitrogen atom to which they are attached, they form an azetidinyl, pyrrolidinyl, piperidinyl, morpholino, thiomorpholino, piperazino or piperazino group substituted on the nitrogen atom by a C$_{1-4}$alkyl group or a C$_{2-4}$alkyl group substituted by a hydroxy or C$_{1-2}$alkoxy group. Particularly preferred heteroaliphatic rings formed by —NR$^9$R$^{10}$ are azetidine, pyrrolidine, piperidine, morpholine, piperazine and N-methylpiperazine, and especially piperidine.

Where the group NR$^9$R$^{10}$ represents a heteroaliphatic ring of 4 to 7 ring atoms substituted by two groups, the first substituent, where present, is preferably selected from hydroxy, CO$_2$R$^e$ (where R$^e$ is hydrogen, methyl, ethyl or benzyl), or C$_{1-2}$alkyl substituted by hydroxy. Where present, the second substituent is preferably a methyl group. Where two substituents are present, said substituents are preferably attached to the same carbon atom of the heteroaliphatic ring.

Where the group NR$^9$R$^{10}$ represents a heteroaliphatic ring of 4 to 7 ring atoms substituted by a spiro-fused lactone ring, particularly preferred examples are:

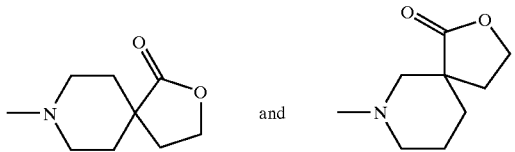

Where the group NR$^9$R$^{10}$ represents a heteroaliphatic ring of 4 to 7 ring atoms and said ring contains a double bond, a particularly preferred group is 3-pyrroline.

Where the group NR$^9$R$^{10}$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where the group NR$^9$R$^{10}$ represents a heteroaliphatic ring of 4 to 7 ring atoms to which is fused a benzene ring or a five membered or six membered nitrogen-containing heteroaromatic ring ring optionally containing 1, 2 or 3 additional heteroatoms selected from N, O and S, said heteroaromatic ring is preferably a five-membered ring, in particular a pyrrole, imidazole or triazole ring, a nitrogen atom of which is preferably included in the heteroaliphatic ring. Suitable examples of such fused ring systems include

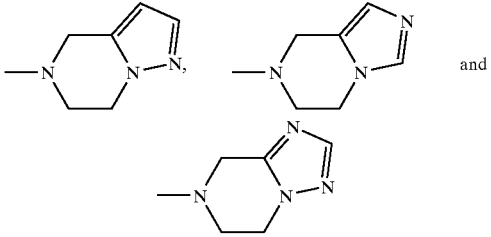

Particularly suitable moieties NR$^9$R$^{10}$ include those wherein NR$^9$R$^{10}$ is amino, methylamino, dimethylamino, diethylamino, azetidino, pyrrolidino, piperidino, morpholino and piperazino.

Where $R^7$ represents an optionally substituted five or six-membered nitrogen-containing heteroaromatic ling optionally containing 1, 2 or 3 additional heteroatoms selected from N, O and S, the heteroaromatic ring is selected from pyrrole, pyridine, pyrazole, imidazole, oxazole, isoxazole, thiazole, isothiazole, pyrazine, pyrimidine, pyridazine, triazole, oxadiazole, thiadiazole, triazine, and tetrazole.

Preferred compounds of the present invention are those wherein $R^7$ is a group selected from imidazole, 1,2,3-triazole and 1,2,4-triazole.

Particularly preferred compounds of the present invention are those wherein $R^7$ is a group selected from imidazol-1-yl and 1,2,4-triazol-1-yl.

Where $R^7$ represents an optionally substituted five membered or six membered nitrogen-containing heteroaromatic ring, preferred substituents are -$ZNR^9R^{10}$ and $C_{1-2}$alkyl (especially methyl). With reference to the group $ZNR^9R^{10}$ defined as a substituent on a heteroaromatic ring in the definition of $R^7$, Z may be a bond or a linear, branched or cyclic group. Favourably Z is a bond or contains 1 to 4 carbon atoms and most favourably 1 to 2 carbon atoms. A particularly favourable group Z is —$CH_2$—. In this instance, particularly suitable moieties $NR^9R^{10}$ include those wherein $NR^9R^{10}$ is amino, methylamino, dimethylamino, diethylamino, azetidino, pyrrolidino, piperidino, morpholino and piperazino. Most especially, -$ZNR^9R^{10}$, as a substituent on a heteroaromatic ring in the definition of $R^7$, is preferably $CH_2N(CH_3)_2$.

A further preferred class of compound of formula (I) is that wherein $R^7$ represents halogen (especially iodine), hydroxy, vinyl, $N_3$ or —$OSO_2R^a$ (especially where $R^a$ is methyl).

Another preferred class of compound of formula (I) is that wherein $R^8$ is hydrogen or methyl, and especially hydrogen.

Another preferred class of compounds of formula (I) is that wherein $R^{12}$ is hydrogen, hydroxy, $C_{1-2}$alkyl substituted by hydroxy, $C_{1-4}$alkoxy (especially methoxy) or $CO_2R^e$ (where $R^e$ is hydrogen, methyl ethyl or benzyl).

A further preferred class of compounds of formula (I) is that wherein $R^{12}$ is hydrogen or $C_{1-4}$alkyl (especially methyl).

$R^{11}$ and $R^{12}$ are preferably attached to the same carbon atom. In particular, when B represents $CH_2$, both hydrogen atoms in said $CH_2$ moiety are replaced by $R^{11}$ and $R^{12}$ forming a moiety of the formula $CR^{11}R^2$.

Where $R^{11}$ and $R^{12}$ are attached to the same carbon atom they may, in particular, together represent —$C(O)OCH_2CH_2$—.

In a further preferred class of compounds of formula (I), $R^{13}$ preferably represents hydrogen, methyl or ethyl. Where A and B both r present $NR^{13}$, each $R^{13}$ substituent is independently defined.

A further preferred class of compound of formula (I) is that wherein n is 1 or 2, and especially wherein n is 1.

One favoured group of compounds of the present invention are of the formula (Ia) and pharmaceutically acceptable salts thereof:

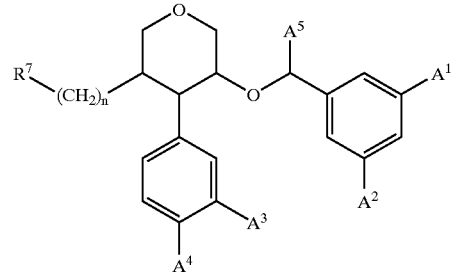

(Ia)

wherein
$A^1$ is fluorine or $CF_3$;
$A^2$ is fluorine or $CF_3$;
$A^3$ is fluorine or hydrogen;
$A^4$ is fluorine or hydrogen;
$A^5$ is methyl; and
$R^7$ and n are as defined in relation to formula (I).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and fluoro$C_{1-6}$alkoxy" means a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

Suitable 5- or 6-membered cyclic ethers include optionally substituted tetrahydropyran and tetrahydrofuran rings.

When used herein the term "halogen" means fluorine, chlorine, bromine and iodine. The most apt halogens are fluorine and chlorine of which fluorine is preferred, unless otherwise stated.

Specific compounds within the scope of this invention include:
(3R)-1-((3R,4S,5S)-5-{(1R)-1-[3,5-bis(trifluoromethyl) phenyl]-ethoxy}-tetrahydro-4-phenylpyran-3-ylmethyl)-3-methylpiperidine-3-carboxylic acid;
(3R)-1-((3S,4S,5S)-5-{(1R)-1-[3,5-bis(trifluoromethyl) phenyl]-ethoxy}-tetrahydro-4-phenylpyran-3-ylmethyl)-3-methylpiperidine-3-carboxylic acid;
(3R)-1-((3S,4R,5S)-5-{(1R)-1-[3,5-bis(trifluoromethyl) phenyl]ethoxy}-tetrahydro-4-phenylpyran-3-ylmethyl)-3-methylpiperidine-3-carboxylic acid;

(3R)-1-((3R,4R,5S)-5-{(1R)-1-[3,5-bis(trifluoromethyl)phenyl]ethoxy}-tetrahydro-4-phenylpyran-3-ylmethyl)-3-methylpiperidine-3-carboxylic acid;

(3R)-1-((3R,4S,5R)-5-{(1R)-1-[3,5-bis(trifluoromethyl)phenyl]ethoxy}-tetrahydro-4-phenylpyran-3-ylmethyl)-3-methylpiperidine-3-carboxylic acid;

(3R)-1-((3S,4S,5R)-5-{(1R)-1-[3,5-bis(trifluoromethyl)phenyl]ethoxy}-tetrahydro-4-phenylpyran-3-ylmethyl)-3-methylpiperidine-3-carboxylic acid;

(3R)-1-((3R,4R,5R)-5-{(1R)-1-[3,5-bis(trifluoromethyl)phenyl]ethoxy}-tetrahydro-4-phenylpyran-3-ylmethyl)-3-methylpiperidine-3-carboxylic acid;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the stereochemistry of the 3-, 4- and 5-positions as shown in formulae (Ib) and (Ic)

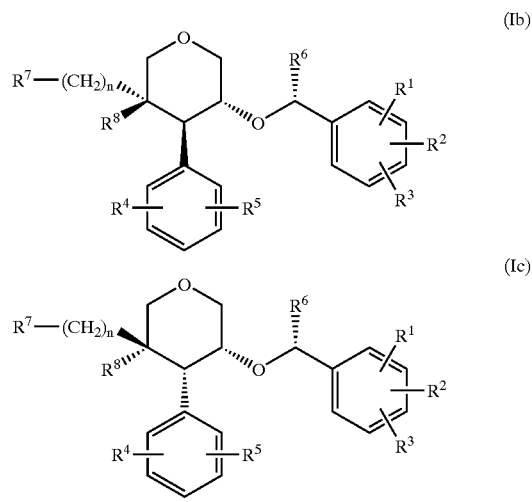

It will be appreciated that the preferred definitions of the various substituents recited herein may be taken alone or in combination and, unless otherwise stated, apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

As used herein, the term "treatment" includes prophylactic use to prevent the occurrence or recurrence of any of the aforementioned conditions.

According to a general process (A), compounds of formula (I), in which $R^7$ is $NR^9R^{10}$ and $R^8$ is hydrogen, may be prepared by the interconversion of a corresponding compound of formula (I) wherein $R^7$ is CHO, $R^8$ is hydrogen and n is zero or 1, hereinafter referred to as formula (II)

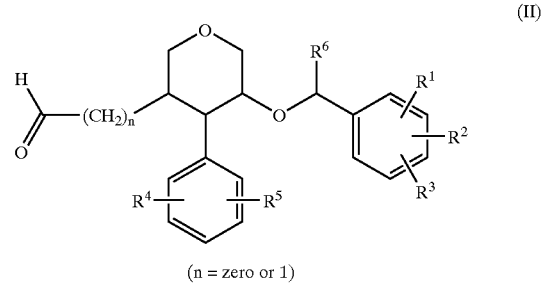

(n = zero or 1)

by reaction with an amine of the formula $HNR^9R^{10}$ in the presence of a reducing agent, for example, sodium triacetoxyborohydride or sodium cyanoborohydride. The reaction is conveniently effected in a suitable solvent such as a halogenated hydrocarbon, for example, 1,2-dichloroethane, conveniently at about room temperature.

According to another general process (B), compounds of formula (I), in which $R^7$ is CHO, $R^8$ is hydrogen and n is zero or 1 (i.e. compounds of formula (II)), may be prepared by interconversion of a corresponding compound of formula (I) in which $R^7$ is hydroxy, $R^8$ is hydrogen and n is 1 or 2, hereinafter referred to as formula (III)

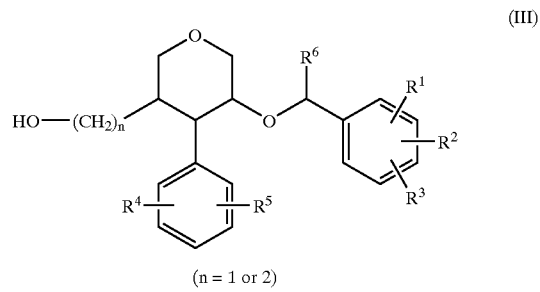

(n = 1 or 2)

The reaction is conveniently effected under conventional conditions suitable for the oxidation of a primary alcohol to an aldehyde without further oxidation to the carboxylic acid, for example, using Dess-Martin periodinane in a suitable solvent such as a halogenated hydrocarbon, for example, dichloromethane, conveniently at about room temperature.

According to another general process (C), compounds of formula (I), in which $R^7$ is hydroxy, $R^8$ is hydrogen and n is 1, may be prepared from a compound of formula (IV)

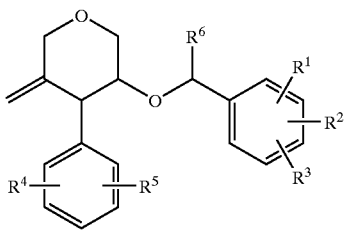

(IV)

by reaction with a reducing agent such as borane.tetrahydrofuran complex, followed by treatment with hydrogen peroxide in the presence of a base such as sodium hydroxide.

According to another general process (D), compounds of formula (I), in which $R^7$ is hydroxy, $R^8$ is hydrogen and n is 1 or 2 (i.e. compounds of formula (III)), may be prepared by the interconversion of a corresponding compound of formula (I) in which $R^7$ is vinyl, $R^8$ is hydrogen and n is zero, hereinafter referred to as formula (V)

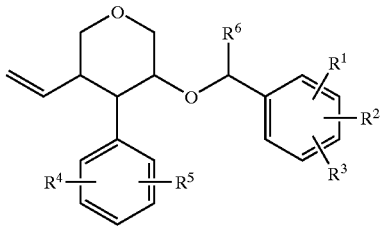

(V)

by reaction with ozone, followed by a reaction with a reducing agent such as sodium borohydride (n is 1), or by reaction with a reducing agent such as borane.tetrahydrofuran complex, followed by hydrogen peroxide in the presence of a base such as sodium hydroxide.

According to another general process (E), compounds of formula (I), in which n is 1, may be prepared by the reaction of a compound of formula (VI)

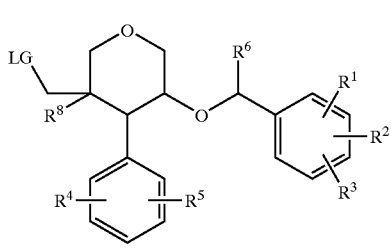

(VI)

wherein LG is a suitable leaving group such as an alkyl- or arylsulfonyloxy group (e.g. mesylate or tosylate) or a halogen atom (e.g. bromine, chlorine or iodine); by reaction with an appropriate amine of the formula $HNR^9R^{10}$, or a heteroaromatic compound suitable for the addition of a five or six-membered nitrogen containing heteroaromatic ring as defined in relation to formula (I), or an azide such as sodium azide.

In each case, the reaction is preferably effected at an elevated temperature, for example, between 40° C. and 80° C., especially between 50° C. and 60° C. The reaction with a heteroaromatic compound is preferably effected in the presence of a suitable organic solvent such as dimethylformamide. The reaction with an azide is preferably effected in the presence of dimethylsulfoxide.

A particularly preferred compound of formula (VI) is that wherein the group LG is mesylate—i.e. a compound of formula (I) in which $R^7$ is the group —$OSO_2CH_3$.

According to a general process (F), compounds of formula (I) in which $R^7$ is a C-linked nitrogen-containing ring wherein A is $NR^{13}$ and B is $CH_2$ may be prepared by the reaction of a compound of formula (XIV)

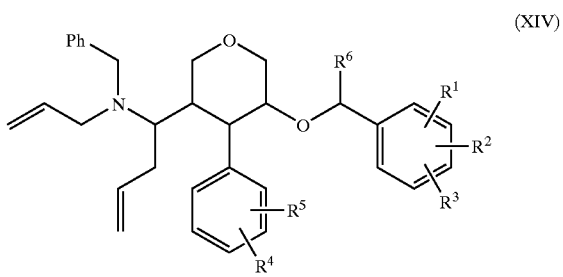

(XIV)

in the presence of a suitable catalyst, and if desired reducing the tetrahydropyridinyl moiety, and also if desired removing or replacing the benzyl moiety.

Suitable catalysts of use in this reaction include any catalyst or multicomponent catalyst system that initiates olefin metathesis. Preferred catalysts are single component metal carbene complexes. Particularly preferred catalysts include:

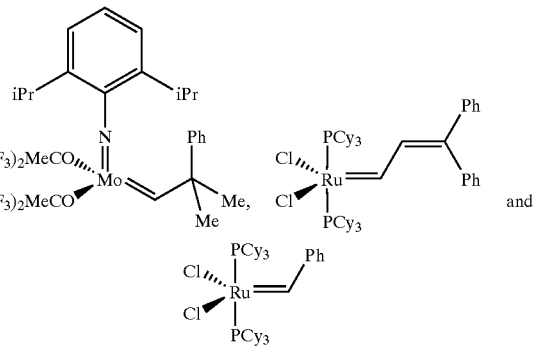

An especially preferred catalyst of use in the present invention is $RuCl_2(PCy_3)_2$=CHPh, also referred to as Grubbs' catalyst. These catalysts and their use is described, for instance, in the following literature:

Bazan et al., *J. Am. Chem. Soc.,* 1991, 113, 6899 and references cited therein.
Nguyen et al., *J. Am. Chem. Soc.,* 1992, 114, 3974.
Nguyen and Grubbs, *J. Organomet. Chem.,* 1995, 497, 195
Schwab et al., *Angew. Chem. Int. Ed. Eng.,* 1995, 34, 2039.
Schwab et al., *J. Am. Chem. Soc.,* 1996, 118, 100.
Grubbs and Chang, *Tetrahedron,* 1998, 54, 4413.

Suitable organic solvents of use in the reaction include halogenated hydrocarbons, such as dichloromethane or chloroform.

The reaction is conveniently effected at room temperature and pressure, for example at about 20° C.

Reduction of the tetrahydropyridinyl moiety may be effected by conventional methodology, for example, by catalytic hydrogenation in the presence of a suitable catalyst such as palladium on carbon, in a suitable solvent such as an alcohol, for example, methanol. These conditions will also conveniently remove the benzyl moiety ($R^{13}$) which may be replaced using conventional methodology.

According to another general process (G), compounds of formula (I) in which $R^7$ is a C-linked nitrogen-containing ring wherein A is $NR^{13}$ and B is a bond may be prepared by the reaction of a compound of formula (XV)

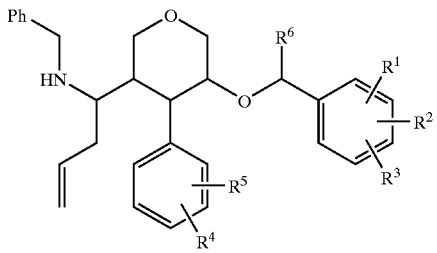

(XV)

under reducing conditions, for instance, in the presence of borane or borane.tetrahydrofuran complex, followed by treatment with hydrogen peroxide and a base such as sodium hydroxide. The reaction is conveniently effected in a solvent such as an ether, for example, tetrahydrofuran.

If desired, the benzyl moiety ($R^{13}$) may be removed as described above.

According to another general process (H), compounds of formula (I) in which $R^7$ is a C-linked nitrogen-containing ring wherein A is $NR^{13}$ and B is O may be prepared by the reaction of a compound of formula (XVI)

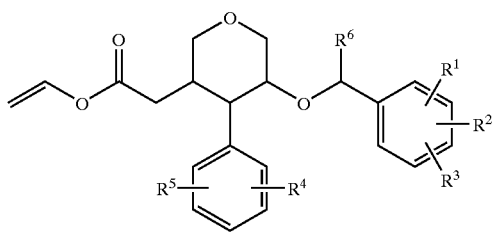

(XVI)

with an amine of the formulae $R^{13}NH_2$, followed by reduction of the keto function using a suitable reducing agent such as a borohydride, for example sodium cyanoborohydride. The reduction is conveniently effected in a solvent such as an ether, for example, tetrahydrofuran.

According to another general process (J), compounds of formula (I) in which $R^7$ is a C-linked nitrogen-containing ring wherein A is O and B is $NR^{13}$ may be prepared by the reaction of a compound of formula (XVII)

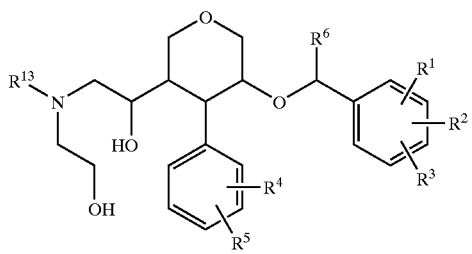

(XVII)

under suitable dehydrating conditions, for example, using triphenylphosphine and diethylazodicarboxylate in a suitable solvent such as tetrahydrofuran, at an elevated temperature such as at reflux, or alternatively using methanesulfonyl chloride or benzenesulfonyl chloride in pyridine or triethylamine, in a suitable organic solvent such as dichloromethane, conveniently at a temperature between room temperature and 80° C.

Further details of suitable procedures will be found in the accompanying Examples.

Compounds of formula (IV) may be prepared by the intramolecular cyclisation of a compound of formula (VII)

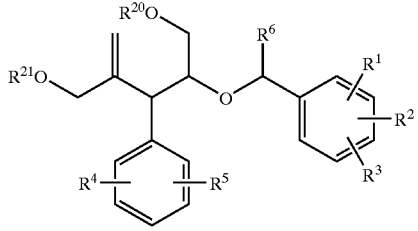

(VII)

wherein $R^{20}O$ is a leaving group such as a sulfonate derivative, for example, mesylate, triflate or, in particular, tosylate, and $R^{21}$ is hydrogen or a hydroxyl protecting group such as a trityl or tert-butyldimethylsilyl group.

Conveniently, when $R^{21}$ is hydrogen, cyclisation is effected by treatment with n-butyl lithium in a suitable solvent such as an ether, for example, tetrahydrofuran, at a reduced temperature, such as between −78° C. and room temperature, for example, at about −78° C., warming to room temperature.

Conveniently, when $R^{21}$ is a tert-butyldimethylsilyl protecting group, deprotection and cyclisation may be effected by treatment with tetrabutylammonium fluoride in a suitable solvent such as an ether, for example, tetrahydrofuran, followed by treatment with 4-(dimethylamino)pyridine, in the presence of an organic base such as a trialkylamine, for example, triethylamine.

It will be appreciated that where $R^{21}$ represents a hydroxyl protecting group such as trityl, such protecting groups may be removed in a conventional manner using, for example, an acid such as trifluoroacetic acid in a suitable solvent, such as a halogenated hydrocarbon, for example, dichloromethane.

In compounds of formula (VII), the leaving group is introduced in a conventional manner by reaction of a corresponding alcohol (i.e. a compound of formula (VII) in which $R^{20}$ is replaced by hydrogen and $R^{21}$ is a protecting group) with a suitable reagent for adding the leaving group. Thus, for example, where $R^{20}$ is tosyl, the corresponding alcohol is reacted with tosyl chloride in the presence of an organic base such as a trialkylamine, for example, triethylamine, and 4-(dimethylamino)pyridine, in a suitable solvent such as a halogenated hydrocarbon, for example, dichloromethane.

The alcohol precursors to the compounds of formula (VII) ($R^{20}$ is hydrogen) are conveniently prepared by the reduction of a compound of formula (VIII)

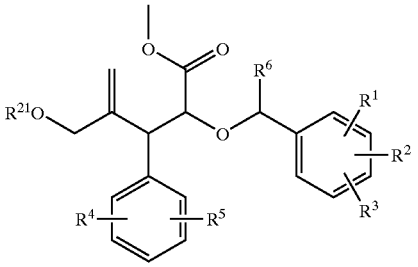

(VIII)

Suitable reducing conditions include the use of a hydride such as diisobutylaluminium hydride at a reduced temperature such as between about −78° C. to room temperature, for example at about −78° C., warming to room temperature. The reaction is conveniently effected in a solvent such as a halogenated hydrocarbon, for example, dichloromethane.

Compounds of formula (VIII) may be prepared by an intramolecular rearrangement of a compound of formula (IX)

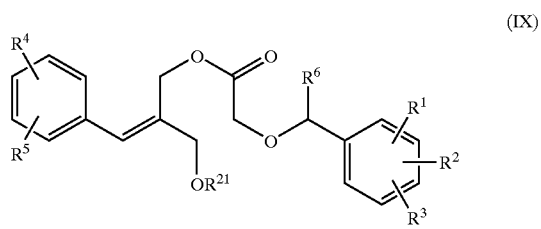
(IX)

The rearrangement is effected by treatment of the compound of formula (IX) with trimethylsilyl chloride and lithium bis(trimethylsilyl)amide in a suitable solvent such as an ether, for example, tetrahydrofuran. The reaction is conveniently effected at a reduced temperature such as between about −78° C. and room temperature, for example, at about −78° C., warming to room temperature. The product of this reaction is then treated with (trimethylsilyl) diazomethane in a suitable solvent such as an alcohol, for example, methanol, or an ether, for example, diethyl ether, or a mixture thereof, conveniently at room temperature.

Compounds of formula (IX) may be prepared by the reaction of a compound of formula (X) with a compound of formula (XI)

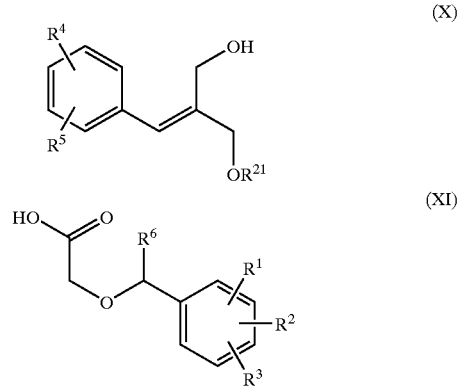
(X)

(XI)

This esterification reaction is effected in a conventional manner, conveniently in the presence of a dehydrating agent or a molecular sieve to remove water from the reaction. Suitable dehydrating agents include dicyclohexylcarbodiimide (DCC), or, more preferably, 1-(3-dimethylaminopropyl)-3-ethylcarbodiimide (EDC), ideally used in the presence of an organic base such as a trialkylamine, for example, triethylamine and a catalytic amount of 4-(dimethylamino) pyridine. The reaction is conveniently effected in a suitable solvent such as a halogenated hydrocarbon, for example, dichloromethane.

Alternatively, the compound of formula (XI) may be converted into the corresponding acyl halide, for example, by reaction with oxalyl chloride, and then the acyl halide is reacted with a compound of formula (X), preferably in the presence of a base, such as an aqueous alkali or, more preferably, in the presence of pyridine. The reaction is conveniently effected in a suitable solvent such as a halogenated hydrocarbon, for example, dichloromethane.

Compounds of formula (X) may be prepared in a conventional manner from known compounds. Suitable methods will be readily apparent to one of ordinary skill in the art, or such methods may be deduced from the examples disclosed herein.

Compounds of formula (XI) may be prepared from a compound of formula (XII)

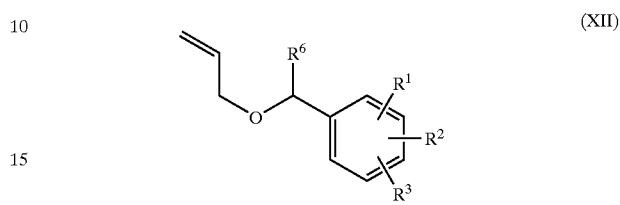
(XII)

by oxidation cleavage using acid dichromate, or acid permanganate, or, more preferably, sodium periodate in the presence of ruthenium tetroxide or, more preferably, ruthenium trichloride hydrate. The reaction is effected in a suitable solvent such as acetonitrile, or a halogenated hydrocarbon, for example, tetrachloromethane, or water, or a mixture thereof.

Compounds of formula (XII) may be prepared from known compounds of formula (XIII)

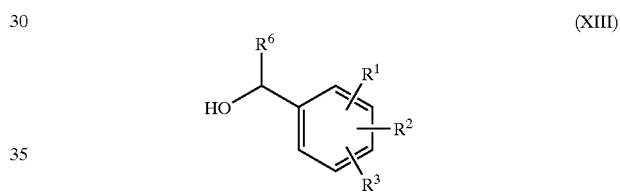
(XIII)

by reaction with an allyl halide, for example, allyl bromide, in the presence of a base such as an alkali metal hydride, for example, sodium hydride. The reaction is conveniently effected in a suitable solvent such as an ether, for example, tetrahydrofuran.

Compounds of formula (V) may be prepared by conventional dehydration methods from, for example, a corresponding compound of formula (I) in which $R^7$ is a hydroxyl group.

Compounds of formula (VI) may be prepared by conventional methods from, for example, a corresponding compound of formula (I) in which $R^7$ is a hydroxyl group. Thus, for example, when LG is a mesylate group a corresponding compound of formula (I) in which $R^7$ is hydroxyl may be reacted with methanesulfonyl chloride in the presence of a base, such as triethylamine. The reaction is conveniently effected in a solvent such as a halogenated hydrocarbon, for example, dichloromethane.

Compounds of formula (XIV) may be prepared from a compound of formula (XV) above, by N-alkylation with an allyl halide, for example, allyl bromide. The reaction is preferably effected in the presence of an inorganic base such as potassium carbonate and a suitable solvent such a dimethylformamide. The reaction is conveniently effected at a temperature between room temperature and 100° C.

Compounds of formula (XV) may be prepared from a compound of formula (XVIII)

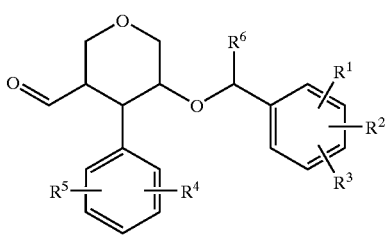

(XVIII)

by reaction with benzylamine in a suitable solvent such as a halogenated hydrocarbon, for example, dichloromethane. Following basification, using for example basic alumina, the reaction mixture is filtered, evaporated and the residue dissolved in a suitable solvent such as an ether, for example, tetrahydrofuran. Reaction with a suitable alkylating reagent such as a Grignard reagent, for example, allyl magnesium bromide, in the presence of a suitable solvent such as an ether, for example, diethyl ether, affords the compound of formula (XV).

Compounds of formula (XVIII) may be prepared from a compound of formula (V) by an ozonolysis reaction, using ozone at a low temperature, for example, between −60° C. and −100° C., in a suitable solvent such as a halogenated hydrocarbon, for example, dichloromethane, or an alcohol, for example, methanol, or a mixture thereof. The intermediate ozonide thus formed need not be isolated but instead is decomposed using a suitable reducing agent, for example, dimethyl sulfide, trimethyl phosphite or thiourea.

Compounds of formula (XVI) may be prepared from a compound of formula (XIX)

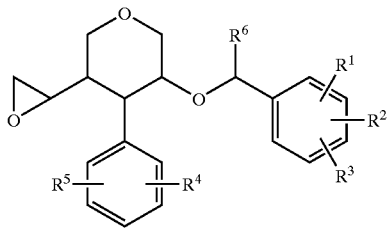

(XIX)

by reaction with allyl alcohol in the presence of a suitable reducing reagent, such as a hydride, for example sodium hydride, in a suitable solvent such as an ether, for example tetrahydrofuran, at an elevated temperature, for example, between 60° C. and 100° C., followed in a second step by an oxidation reaction, for example using a mild oxidizing reagent such as Dess-Martin periodinane, in a suitable solvent such as a halogenated hydrocarbon, for example dichloromethane, conveniently at room temperature.

Compounds of formula (XIX) may be prepared from a compound of formula (V) by an epoxidization reaction using a peracid, for example, m-chloroperbenzoic acid. The reaction is effected in a solvent such as a halogenated hydrocarbon, for example, dichloromethane, conveniently at room temperature.

Compounds of formula (XVII) may be prepared from a compound of formula (XIX) by reaction with a suitable amine of the formula $R^{13}NHCH_2CH_2OH$. The reaction is conveniently effected in a solvent such as an alcohol, for example methanol, at an elevated temperature, for example at the reflux temperature of the solvent.

In an alternative methodology, compounds of formula (IV) may also be prepared by the reduction of a corresponding lactone of formula (XX)

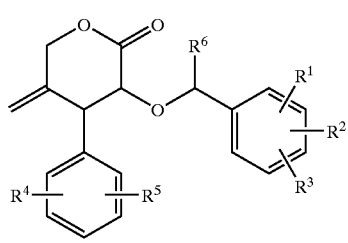

(XX)

Suitable reducing conditions include the use of a hydride such as diisobutylaluminium hydride at a reduced temperature such as between about −78° C. to room temperature, for example at about −78° C., warming to room temperature, followed by treatment with a reagent prepared from $BF_3$-etherate, such as boron trifluoride diethyl etherate. The reactions are conveniently effected in a solvent such as a halogenated hydrocarbon, for example, dichloromethane.

Compounds of formula (XX) may be prepared by the intramolecular cyclisation of a compound of formula (XXI)

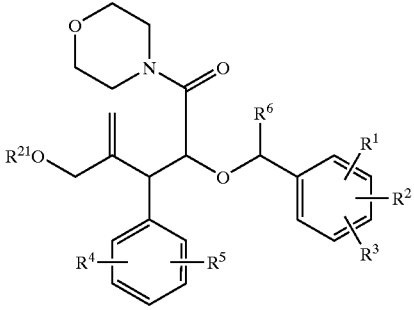

(XXI)

wherein $R^{21}$ is hydrogen or a hydroxyl protecting group such as a trityl or tert-butyldimethylsilyl group. Cyclisation may be conveniently effected by heating at reflux in the presence of ethereal hydrochloric acid followed by azeotropic distillation from toluene.

Compounds of formula (XXI) may be prepared by the reaction of compounds of formula (XXII) and (XXIII)

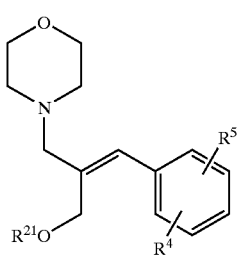

(XXII)

-continued

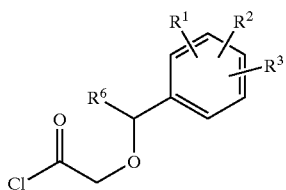

(XXIII)

by a reaction analogous to that described by V. M. Dong and D. W. C. MacMillan in *J. Am. Chem. Soc.,* 2001, 123, 2448–2449.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method.

The following non-limiting Examples serve to illustrate the preparation of compounds of the present invention:

DESCRIPTION 1

(E)-2-Formyloxymethyl-3-phenylacrylic acid methyl ester

To a stirred solution of triethylammonium formate (1.87 g) in acetonitrile (4 ml) was added (Z)-2-bromomethyl-3-phenylacrylic acid methyl ester (1.30 g) and the mixture heated at reflux for 2 hours. The reaction was cooled and extracted into diethyl ether (3×10 ml). The combined organics were dried ($MgSO_4$) and concentrated under reduced pressure to afford the title compound as a crude oil.

$^1$H NMR ($CDCl_3$, 400 MHz): δ 3.85 (3H, s), 5.05 (2H, s), 7.37–7.44 (5H, m), 8.03 (1H, s), 8.16 (1H, s).

DESCRIPTION 2

(E)-2-Hydroxymethyl-3-phenylacrylic acid methyl ester

One drop of concentrated hydrochloric acid was added to a solution of the crude product from Description 1 (1.05 g) in methanol (5 ml) and stirred at ambient temperature for 60 minutes. The reaction was diluted with diethyl ether, dried over $MgSO_4$ and concentrated under reduced pressure to give a crude oil which was purified on silica eluting with 85% ethyl acetate/iso-hexane to afford the title compound as a pale yellow oil.

$^1$H NMR ($CDCl_3$, 400 MHz): δ 3.87 (3H, s), 4.49 (2H, s), 7.37–7.47 (5H, m), 7.84 (1H, s).

DESCRIPTION 3

(E)-2-(tert-Butyldimethylsilyloxymethyl)-3-phenylacrylic acid methyl ester

The product from Description 2 (550 mg) was added to a stirred solution of imidazole (486 mg) in N,N-dimethylformamide (1 ml). tert-Butyl(dimethyl)silyl chloride (517 mg) in N,N-dimethylformamide (1 ml) was then added and the mixture left to stir at ambient temperature for 16 hours. The reaction was diluted with diethyl ether and washed with hydrochloric acid (1M), saturated $NaHCO_3$ solution and brine. The organics were dried over $MgSO_4$ and concentrated under reduced pressure to afford the title compound as a crude oil.

$^1$H NMR ($CDCl_3$, 360 MHz): δ 0.11 (6H, s), 0.92 (9H, s), 3.82 (3H, s), 4.46 (2H, s), 7.36–7.39 (3H, s), 7.59 (2H, dd, J 7.7, 2.2 Hz), 7.83 (1H, s).

DESCRIPTION 4

(Z)-2-(tert-Butyldimethylsilyloxymethyl)-3-phenylprop-2-n-1-ol

The crude product from Description 3 was dissolved in dichloromethane (30 ml), cooled to −78° C. and, with stirring, diisobutylaluminium hydride (1M solution in hexanes, 8.31 ml) was added over a period of 15 minutes. After 1 hour, the reaction was quenched with potassium sodium tartrate (0.5M) and diluted with diethyl ether (20 ml). The solution was left to warm to ambient temperature before diluting with a further 50 ml of a potassium sodium tartrate (0.5M). The heterogenous mixture was then stirred vigorously until both phases were clear. The organics were dried (brine, $MgSO_4$) and concentrated under reduced pressure to afford the title compound as a crude oil.

$^1$H NMR ($CDCl_3$, 360 MHz): δ 0.07 (6H, s), 0.92 (9H, s), 4.36 (2H, s), 4.50 (2H, s), 6.63 (1H, s), 7.20–7.29 (3H, m), 7.34–7.39 (2H, m).

DESCRIPTION 5 tert-Butyldimethylsilyl (Z)-3-phenyl-2-trityloxymethylprop-2-enyl ether

To a stirred solution of the product from Description 4 (1.00 g) in dichloromethane (48 ml) was added triethylamine (1.02 ml), 4-(dimethylamino)pyridine (30 mg) and triphenylmethyl chloride (1.44 g). After 16 hours the reaction was concentrated under reduced pressure to afford a crude oil. This was purified on silica eluting with 3% ethyl acetate/iso-hexane to afford the title compound as a pale yellow oil.

$^1$H NMR ($CDCl_3$, 400 MHz): δ −0.12 (6H, s), 0.76 (9H, s), 3.82 (2H, d, J 6.5 Hz), 4.28 (2H, s), 6.88 (1H, s), 7.11–7.51 (20H, m).

DESCRIPTION 6

(E)-3-Phenyl-2-trityloxymethylprop-2-en-1-ol

To a stirred solution of the product from Description 5 (1.83 g) in tetrahydrofuran (50 ml) was added tetrabutylammonium fluoride (1M solution in tetrahydrofuran, 3.94 ml). After 30 minutes, the reaction was diluted with diethyl ether and washed with hydrochloric acid (1M), saturated $NaHCO_3$ solution and brine before drying over $MgSO_4$ and concentrating under reduced pressure to afford the title compound as a crude oil.

$^1$H NMR ($CDCl_3$, 400 MHz): δ 2.17–2.22 (1H, m), 3.91 (2H, d, J 1.1 Hz), 4.28 (2H, d, J 5.1 Hz), 6.67 (1H, s), 7.22–7.51 (20H, m).

DESCRIPTION 7

Allyl (1R)-1-[3,5-bis(trifluoromethyl)phenyl]ethyl ether

To a stirred solution of (1R)-1-[3,5-bis(trifluoromethyl) phenyl]ethanol (5.00 g) in tetrahydrofuran (20 ml) at 0° C.

was added sodium hydride (60% dispersion in mineral oil, 1.16 g). After 30 minutes, allyl bromide (3.35 ml) was added and the mixture refluxed for 16 hours. The reaction was quenched by careful addition of saturated NH$_4$Cl solution at 0° C. and diluted with diethyl ether. The organics were dried (brine, MgSO$_4$) and concentrated under reduced pressure to afford the title compound as a crude oil.

$^1$H NMR (CDCl$_3$, 400 MHz): δ 1.48 (3H, d, J 6.4 Hz), 3.85–3.95 (2H, m), 4.60 (1H, q, J 6.4 Hz), 5.20 (1H, dq, J 10.3, 1.2 Hz), 5.26 (1H, dq, J 17.2, 1.6 Hz), 5.86–5.95 (1H, m), 7.78 (3H, s).

DESCRIPTION 8

{(1R)-1-[3,5-Bis(trifluoromethyl)phenyl] ethoxy}acetic acid

To a stirred solution of the product from Description 7 (3.00 g) in a mixture of tetrachloromethane (20 ml), acetonitrile (20 ml) and water (30 ml) was added sodium periodate (8.62 g). Ruthenium trichloride hydrate (50 mg) was then added and the mixture stirred for 1 hour. The reaction was extracted into dichloromethane and the combined organics dried (brine, MgSO$_4$) and concentrated under reduced pressure. The resulting residue was taken up in diethyl ether and filtered through Hyflo™ before concentrating under reduced pressure to afford the title compound as a crude black oil.

$^1$H NMR (CDCl$_3$, 360 MHz): δ 1.56 (3H, d, J 6.5 Hz), 4.06 (2H, q, J 16.1 Hz), 4.72 (1H, d, J 6.5 Hz), 7.80 (2H, s), 7.83 (1H, s).

DESCRIPTION 9

{(1R)-1-[3,5-Bis(trifluoromethyl)phenyl] ethoxy}acetic acid (Z)-2-(tert-butyldimethylsilyloxymethyl)-3-phenylprop-2-enyl ester To a stirred solution of the product from Description 4 (850 mg) in dichloromethane (15 ml), the product from Description 8 (665 mg) was added followed by 1-(3-dimethylaminopropyl)-3-ethylcarbodiimide (608 mg), triethylamine (442 µl) and a catalytic amount of 4-(dimethylamino)pyridine. After 16 hours, a further 200 mg of the product from Description 6, 160 mg of 1-(3-dimethylaminopropyl)-3-ethylcarbodiimide, 100 µl of triethylamine and a catalytic amount of 4-(dimethylamino) pyridine, were added and stirring continued until complete consumption of the product from Description 4 was observed by thin layer chromatography. The reaction was diluted with diethyl ether (50 ml) and washed with hydrochloric acid (1M), saturated NaHCO$_3$ solution and brine before drying over MgSO$_4$ and concentrating under reduced pressure to give a crude oil. This was purified on silica eluting with 5% ethyl acetate/iso-hexane to afford the title compound as a pale yellow oil.

$^1$H NMR (CDCl$_3$, 400 MHz): δ 0.01 (6H, s), 0.87 (9H, s), 1.55 (3H, d, J 6.4 Hz), 3.99 (1H, d, J 16.4 Hz), 4.13 (1H, d, J 16.4 Hz), 4.32 (2H, s), 4.74 (1H, q, J 6.4 Hz), 4.87 (2H, s), 6.65 (1H, s), 7.21–7.34 (5H, m), 7.81 (3H, s).

DESCRIPTION 10

(2S,3S)-2-{(1R)-1-[3,5-Bis(trifuoromethyl)phenyl] ethoxy}-4-(tert-butyldimethylsilyloxymethyl)-3-phenylpent-4-enoic acid methyl ester To a stirred solution of the compound from Description 9 (300 mg) in tetrahydrofuran (15 ml) at −78° C. was added trimethylsilyl chloride (1M solution in tetrahydrofuran, 2.18 ml). After 5 minutes, lithium bis(trimethylsilyl)amide (1M solution in tetrahydrofuran, 2.08 ml) was added rapidly and the reaction left for 10 minutes before allowing to warm to ambient temperature over 1 hour. The mixture was quenched with saturated NH$_4$Cl solution (10 ml), stirred for 2 hours and partitioned between diethyl ether (15 ml) and hydrochloric acid (1M, 15 ml). The reaction was extracted with diethyl ether (×2) and the combined organics dried over MgSO$_4$ and concentrated under reduced pressure to afford a crude oil. This was dissolved in a mixture of methanol (1 ml) and diethyl ether (4 ml) and (trimethylsilyl)diazomethane (2M solution in hexanes, 1.04 ml) was added with stirring. The reaction was concentrated under reduced pressure to give a crude mixture of four diastereomers in the following ratio:

(2R,3S)-1 (2S,3R)-2

(2R,3R)-2 (2S,3S)-9

This mixture was purified on silica eluting with 3% ethyl acetate/iso-hexane to afford the title compound as a pale yellow oil.

$^1$H NMR (CDCl$_3$, 360 MHz): δ −0.04 (3H, s), −0.03 (3H, s), 0.86 (9H, s), 1.13 (3H, d, J 6.5 Hz), 3.47 (3H, s), 3.73 (1H, d, J 9.4 Hz), 3.91–4.01 (2H, m), 4.24–4.33 (2H, m), 5.07 (1H, s), 5.26 (1H, s), 7.27–7.35 (5H, m), 7.63 (2H, s), 7.74 (1H, s).

DESCRIPTION 11

(2S,3S)-2-{(1R)-1-[3,5-Bis(trifluoromethyl) phenyl}ethoxy-4-(tert-butyldimethylsilyloxymethyl)-3-phenylpent-4-en-1-ol To a stirred solution of the product from Description 10 (550 mg) in dichloromethane (20 ml) at −78° C. was added diisobutylaluminium hydride (1M solution in dichloromethane, 3.00 ml) over 15 minutes. The solution was stirred for 30 minutes before allowing to warm to ambient temperature over 2 hours and then quenched at 0° C. with potassium sodium tartrate (0.5M) and diluted with diethyl ether (20 ml). The solution was left to warm to ambient temperature before diluting with a further 40 ml of potassium sodium tartrate (0.5M). The heterogenous mixture was then stirred vigorously until both phases were clear. The organics were dried (brine, MgSO$_4$) and concentrated under reduced pressure to afford a crude oil which was purified on silica eluting with 5% ethyl acetate/iso-hexane to afford the title compound as a pale yellow oil.

$^1$H NMR (CDCl$_3$, 360 MHz): δ 0.02 (6H, s), 0.88 (9H, s), 0.98 (3H, d, J 6.4 Hz), 3.57–3.65 (2H, m), 3.67–3.73 (1H, m), 3.87–3.91 (1H, m), 3.93–4.03 (2H, m), 4.08–4.15 (1H, m), 5.09 (1H, s), 5.27 (1H, s), 7.28–7.39 (5H, m), 7.61 (2H, s), 7.74 (1H, s).

DESCRIPTION 12

Toluene-4-sulfonic acid (2S,3S)-2-{(1R)-1-[3,5-bis (trifluoromethyl)phenyl]-ethoxy}-4-(tert-butyldimethylsilyloxymethyl)-3-phenylpent-4-enyl ester To a stirred solution of the product from Description 11 (60 mg) in dichloromethane (2 ml) at 0° C. was added triethylamine (23 µl), 4-(dimethylamino)pyridine (16.1 mg) and p-toluenesulfonyl chloride (31.3 mg). After 30 minutes, the reaction was allowed to warm to ambient temperature and stirred for a further 24 hours. The mixture was diluted with dichloromethane and washed with hydrochloric acid (1M), saturated NaHCO$_3$ solution and brine before drying over MgSO$_4$ and concentrating under reduced pressure to afford the title compound as a crude oil.

$^1$H NMR (CDCl$_3$, 360 MHz): δ −0.03 (3H, s), −0.02 (3H, s), 0.85 (9H, s), 0.90 (3H, d, J 6.4 Hz), 2.41 (3H, s), 3.43 (1H, d, J 9.7 Hz), 3.88–3.93 (3H, m), 4.14–4.22 (2H, m), 4.28 (1H, q, J 6.4 Hz), 5.04 (1H, s), 5.23 (1H, s), 7.23–7.31 (7H, m), 7.51 (2H, s), 7.60 (2H, d, J 8.3 Hz), 7.71 (1H, s).

DESCRIPTION 13

(3S,4S)-3-{(1R)-1-[3,5-Bis(trifluoromethyl)phenyl]ethoxyl}-tetrahydro-5-methylene-4-phenylpyran To a stirred solution of the product from Description 12 (70 mg) in tetrahydrofuran (2 ml) was added tetrabutylammonium fluoride (1M solution in tetrahydrofuran, 110 μl). After 30 minutes, triethylamine (23 μl) and 4-(dimethylamino)pyridine (16 mg) was added and the mixture left to stir for 16 hours. The reaction was diluted with diethyl ether and washed with 1M hydrochloric acid, saturated NaHCO$_3$ solution and brine before drying over MgSO$_4$ and concentrating under reduced pressure to give a crude oil which was purified on silica eluting with ethyl acetate/iso-hexane to afford the title compound as a pale yellow oil.

$^1$H NMR (CDCl$_3$, 400 MHz): δ 1.03 (3H, d, J 6.5 Hz), 3.54 (1H, d, 9.4 Hz), 4.03 (2H, s), 4.08–4.18 (1H, m), 4.28–4.56 (3H, m), 5.15 (1H, s), 5.33 (1H, s), 7.28–7.39 (5H, m), 7.62 (2H, s), 7.73 (1H, s).

DESCRIPTION 14

{(1R)-1-[3,5-Bis(trifluoromethyl)phenyl]ethoxy}acetic acid (Z)-3-phenyl-2-trityloxymethylallyl ester To a stirred solution of the product from Description 8 (1.82 g) in dichloromethane (5 ml) was added one drop of N,N-dimethylformamide and oxalyl chloride (731 μl). After 1 hour, the reaction was concentrated under reduced pressure and taken up in 10 ml of dichloromethane. This was added to a stirred solution of the product from Description 6 (1.80 g) in pyridine (498 μl) and dichloromethane (10 ml). After 30 minutes, the reaction was washed with hydrochloric acid (1M), saturated NaHCO$_3$ solution and brine before drying over MgSO$_4$ and concentrating under reduced pressure to give a crude oil. This was purified on silica eluting with 10% ethyl acetate/iso-hexane to afford the title compound as a pale yellow oil.

$^1$H NMR (CDCl$_3$, 400 MHz): δ 1.47 (3H, d, J 6.5 Hz), 3.77 (1H, d, J 16.4 Hz), 3.78 (2H, d, J 1.1 Hz), 3.94 (1H, d, J 16.4 Hz), 4.58 (1H, q, J 6.5 Hz), 4.84 (2H, s), 6.90 (1H, s), 7.20–7.47 (20H, m), 7.74 (2H, s), 7.80 (1H, s).

DESCRIPTION 15

(2RS,3RS)-2-{(1R)-1-[3,5-Bis(trifluoromethyl)phenyl]ethoxy}-3-phenyl-4-trityloxymethylpent-4-enoic acid methyl ester To a stirred solution of the compound from Description 14 (500 mg) in tetrahydrofuran (20 ml) at −78° C. was added trimethylsilyl chloride (1M solution in tetrahydrofuran, 2.98 ml). After 5 minutes, lithium bis(trimethylsilyl)amide (1M solution in tetrahydrofuran, 2.84 ml) was added rapidly and the reaction left for 10 minutes before allowing to warm to ambient temperature over 1 hour. The mixture was quenched with saturated NH$_4$Cl solution (10 ml), stirred for 2 hours and partitioned between diethyl ether (15 ml) and hydrochloric acid (1M, 15 ml). The reaction was extracted with diethyl ether (×2) and the combined organics dried over MgSO$_4$ and concentrated under reduced pressure to afford a crude oil. This was dissolved in a mixture of methanol (1 ml) and diethyl ether (4 ml) and (trimethylsilyl)diazomethane (2M solution in hexanes, 3.00 ml) was added with stirring. The reaction was concentrated under reduced pressure to afford a crude oil which was purified on silica eluting with 3% ethyl acetate/iso-hexane to afford the title compound as a mixture of four diastereomers. $^1$H NMR (CDCl$_3$, 400 MHz) was used to determine their relative ratio (the diagnostic signal is the doublet corresponding to the methyl of the 2-ethoxy substituent):

(2R,3S)-3 δ 1.43 (3H, d, J 6.4 Hz)
(2R,3R)-1 δ 1.35 (3H, d, J 6.5 Hz)
(2S,3R)-6 δ 1.23 (3H, d, J 6.4 Hz)
(2S,3S)-3 δ 1.08 (3H, d, J 6.4 Hz)

DESCRIPTIONS 16a AND 16b

(a) (2S,3RS)-2-{(1R)-1-[3,5-Bis(trifluoromethyl)phenyl]ethoxy}-3-phenyl-4-trityloxymethylpent-4-en-1-ol

(b) (2R,3RS)-2-{(1R)-1-[3,5-Bis(trifluoromethyl)phenyl]ethoxy}-3-phenyl-4-trityloxymethylpent-4-en-1-ol To a stirred solution of the product from Description 15 (5.50 g) in dichloromethane (100 ml) at −78° C. was added diisobutylaluminium hydride (1M solution in dichloromethane, 22.9 ml) over 15 minutes. The solution was stirred for 30 minutes before allowing to warm to ambient temperature over 2 hours and then quenched at 0° C. with a 0.5M solution of potassium sodium tartrate and diluted with diethyl ether (50 ml). The solution was left to warm to ambient temperature before diluting with a further 50 ml of a 0.5M solution of potassium sodium tartrate. The heterogenous mixture was then stirred vigorously until both phases were clear. The organics were dried (brine, MgSO$_4$) and concentrated under reduced pressure to afford a crude oil which was purified on silica eluting with 10% ethyl acetate/iso-hexane to afford the title compounds as two discrete mixtures of diastereomers:

Description 16a: less polar mixture of 2 diastereomers (2S,3R) & (2S,3S) in a 2:1 ratio:

Signals for (2S,3R) isomer $^1$H NMR (CDCl$_3$, 400 MHz): δ 1.25 (3H, d, J 6.3 Hz), 3.25 (1H, dd, J 11.7, 5.1 Hz), 3.44 (1H, dd, J 11.7, 4.3 Hz), 3.58 (2H, d, J 3.9 Hz), 3.61–3.64 (1H, m), 3.81–3.85 (1H, m), 4.42 (1H, q, J 6.3 Hz), 5.47 (1H, s), 5.59 (1H, d, J 1.6 Hz), 7.15–7.41 (20H, m), 7.66 (2H, s), 7.76 (1H, s).

Signals for (2S,3S) isomer $^1$H NMR (CDCl$_3$, 400 MHz): δ 0.93 (3H, d, J 6.7 Hz), 3.53 (2H, d, J 3.9 Hz), 3.61–3.64 (1H, m), 3.66–3.68 (2H, m), 3.88–3.93 (1H, m), 4.08–4.13 (1H, m), 5.14 (1H, m), 5.40 (1H, d, J 1.2 Hz), 7.15–7.41 (20H, m), 7.58 (2H, s), 7.73 (1H, s).

Description 16b: more polar mixture of 2 diastereomers (2R,3S) & (2R,3R) in a 9:2 ratio:

Signals for (2R,3S) $^1$H NMR (CDCl$_3$, 400 MHz): δ 1.39 (3H, d, J 6.3 Hz), 3.41–3.47 (1H, m), 3.49 (2H, s), 3.54 (1H, d, J 7.4 Hz), 3.73 (1H, dd, J 12.1, 4.3 Hz), 3.85–3.89 (1H, m), 4.60 (1H, q, J 6.3 Hz), 5.09 (1H, s), 5.35 (1H, d, J 1.1 Hz), 7.01–7.03 (2H, m), 7.13–7.14 (3H, m), 7.19–7.87 (15H, m), 7.63 (2H, s), 7.76 (1H, s).

Diagnostic signals for (2R,3R) $^1$H NMR (CDCl$_3$, 400 MHz): δ 1.33 (1H, d, J 6.7 Hz), 4.26 (1H, q, J 6.7 Hz).

DESCRIPTION 17

Toluene-4-sulfonic acid (2S,3RS)-2-{(1R)-1-[3,5-bis(trifluoromethyl)phenyl]ethoxy}-3-phenyl-4-trityloxymethylpent-4-enyl ester To a stirred solution of Description 16a (3.18 g) in dichloromethane (90 ml) at 0° C. was added triethylamine (962 μl), 4-(dimethylamino)pyridine (675 mg) and p-toluenesulfonyl chloride (1.31 g). After 30 minutes, the reaction was allowed to warm to ambient temperature and stirred for a further 24 hours. The mixture was diluted with dichloromethane and washed with 1M hydrochloric acid, saturated $NaHCO_3$ solution and brine before drying over $MgSO_4$ and concentrating under reduced pressure to afford the title compounds as a mixture of two diastereomers (2S,3R) & (2S,3S) in a 2:1 ratio:

Diagnostic signals for (2S,3R) isomer: $^1$H NMR ($CDCl_3$, 400 MHz): δ 1.12 (3H, d, J 6.7 Hz), 5.40 (1H, s), 5.53 (1H, d, J 1.2 Hz).

Diagnostic signals for (2S,3S) isomer: $^1$H NMR ($CDCl_3$, 400 MHz): δ 0.86 (3H, d, J 6.3 Hz), 5.11 (1H, s), 5.83 (1H, s).

DESCRIPTION 18

Toluene-4-sulfonic acid (2R,3RS)-2-{(1R)-1-[3,5-bis(trifluoromethyl)phenyl]ethoxy}-3-phenyl-4-trityloxymethylpent-4-enyl ester Prepared according tot he method of Description 17 using Description 16b, to afford the title compounds as a mixture of two diastereomers (2R,3S) & (2R,3R) in a 5:1 ratio:

Diagnostic signals for (2R,3S) isomer: $^1$H NMR ($CDCl_3$, 400 MHz): δ 1.31 (3H, d, J 6.3 Hz), 4.51 (1H, q, J 6.3 Hz).

Diagnostic signals for (2R,3R) isomer: $^1$H NMR ($CDCl_3$, 400 MHz): δ 1.26 (3H, d, J 6.3 Hz), 4.25 (1H, d, J 6.3 Hz).

DESCRIPTIONS 19a AND 19b (a) Toluene-4-sulfonic acid (2S,3R)-2-{(1R)-1-[3,5-bis(trifluoromethyl)-phenyl]ethoxy}-4-hydroxymethyl-3-phenylpent-4-enyl ester (b) Toluene-4-sulfonic acid (2S,3S)-2-{(1R)-1-[3,5-bis(trifluoromethyl)-phenyl]ethoxy}-4-hydroxymethyl-3-phenylpent-4-enyl ester The product from Description 17 (3.80 g) was stirred in a 5% trifluoroacetic acid/dichloromethane (50 ml) solution at 0° C. for 1 hour. 50 ml of saturated $NaHCO_3$ solution was added and the organic phase washed with brine before drying over $MgSO_4$ and concentrating under reduced pressure to afford a crude solid. This was purified on silica eluting with 10–40% ethyl acetate/iso-hexane to afford a yellow oil which was further purified by LOBAR® eluting with 33% ethyl acetate/iso-hexane to afford the discrete diastereomeric title compounds as yellow oils:

Description 19a, (2S,3R), less polar: $^1$H NMR ($CDCl_3$, 400 MHz): δ 1.24 (3H, d, J 6.7 Hz), 3.05 (3H, s), 3.64 (1H, d, J 7.0 Hz), 3.67 (1H, dd, J 10.6, 5.9 Hz), 3.98–4.05 (3H, m), 4.11–4.15 (2H, m), 4.48 (1H, dd, J 12.9, 6.3 Hz), 5.37 (2H, s), 7.19–7.32 (7H, m), 7.49–7.52 (2H, m), 7.65 (2H, s), 7.75 (1H, s).

Description 19b, (2S,3S), more polar: $^1$H NMR ($CDCl_3$, 400 MHz): δ 0.92 (3H, d, J 6.7 Hz), 2.42 (3H, s), 3.54 (1H, d, J 9.8 Hz), 3.94–4.02 (3H, m), 4.14–4.20 (2H, m), 4.30 (1H, q, 6.3 Hz), 5.10 (1H, s), 5.29 (1H, t, J 1.2 Hz), 7.24–7.33 (7H, m), 7.52 (2H, s), 7.59–7.62 (2H, m), 7.70 (1H, s).

DESCRIPTIONS 20a AND 20b (a) Toluene-4-sulfonic acid (2R,3S)-2-{(1R)-1-[3,5-bis(trifluoromethyl)phenyl]ethoxy}-4-hydroxymethyl-3-phenylpent-4-enyl ester (b) Toluene-4-sulfonic acid (2R,3R)-2-{(1R)-1-[3,5-bis(trifluoromethyl)phenyl]ethoxy}-4-hydroxymethyl-3-phenylpent-4-enyl ester By analogy with Description 19 using the product from Description 18 to afford a crude yellow solid which was purified by LOBAR® eluting with 33% ethyl acetate/iso-hexane to afford the discrete diastereomeric title compounds as yellow oils:

Description 20a, (2R,3S), less polar: $^1$H NMR ($CDCl_3$, 400 MHz): δ 1.41 (3H, d, J 6.3 Hz), 2.45 (3H, s), 3.52 (1H, d, J 7.4 Hz), 3.92 (1H, d, J 7.4 Hz), 3.92–4.00 (4H, m), 4.17 (1H, dd, J 10.2, 2.7 Hz), 4.63 (1H, q, J 6.3 Hz), 5.00 (1H, s), 5.14 (1H, s), 7.00–7.03 (2H, m), 7.13–7.26 (3H, m), 7.31 (2H, d, J 8.2 Hz), 7.58 (2H, s), 7.68–7.71 (2H, m), 7.76 (1H, s).

Description 20b, (2R,3R), more polar: $^1$H NMR ($CDCl_3$, 400 MHz): δ 1.29 (3H, d, J 6.7 Hz), 2.47 (3H, s), 3.84 (2H, s), 4.08–4.17 (2H, m), 4.31 (1H, q, J 6.7 Hz), 4.40 (1H, dd, J 9.8, 1.6 Hz), 4.99 (1H, s), 5.18 (1H, s), 7.02–7.28 (7H, m), 7.87 (2H, dd, J 8.6, 0.8 Hz), 7.66 (1H, s), 7.81–7.83 (2H, m).

DESCRIPTION 21

(3S,4R)-3-{(1R)-1-[3,5-bis(trifluoromethyl)phenyl]ethoxy}-tetrahydro-5-methylene-4-phenylpyran To a stirred solution of Description 19a (1.30 g) in tetrahydrofuran (25 ml) at –78° C. was added n-butyllithium (1.6M solution in hexanes, 1.6 ml) in small portions and the mixture left to warm to ambient temperature over 16 hours. The reaction was quenched with hydrochloric acid (2M, 2 ml) and neutralised with saturated $NaHCO_3$ solution before extracting into ethyl acetate (2×50 ml). The combined organics were dried (brine, $MgSO_4$) and concentrated under reduced pressure to afford the title compound as a crude oil which crystallise on standing.

$^1$H NMR ($CDCl_3$, 400 MHz): δ 1.33 (3H, d, J 6.7 Hz), 3.64–3.61 (2H, m), 3.67 (1H, d, J 2.8 Hz), 3.75 (1H, dd, J 12.3, 2.8 Hz), 4.08 (1H, d, J 12.6 Hz), 4.24 (1H, q, J 6.7 Hz), 4.36 (1H, d, J 12.6 Hz), 4.80 (1H, d, J 0.7 Hz), 5.08 (1H, s), 7.14–7.43 (3H, m), 7.52–7.55 (2H, m), 7.76 (1H, s), 7.80 (2H, s).

DESCRIPTION 22

(3R,4S)-3-{(1R)-1-[3,5-bis(trifluoromethyl)phenyl]ethoxy}-tetrahydro-5-methylene-4-phenylpyran By analogy with Description 21 using Description 20a to afford the title compound as a yellow oil.

$^1$H NMR ($CDCl_3$, 360 MHz): δ 1.48 (3H, d, J 6.7 Hz), 3.43 (1H, s), 3.59 (1H, d, J 2.1 Hz), 3.65 (1H, dd, J 3.7, 1.4 Hz), 4.12 (1H, d, J 13.0 Hz), 4.25 (1H, dd, J 12.6, 2.8 Hz), 4.39 (1H, d, 13.0 Hz), 4.62 (1H, q, J 6.3 Hz), 4.75 (1H, d, J 2.1 Hz), 5.03 (1H, s), 7.26–7.31 (3H, m), 7.36–7.42 (4H, m), 7.65 (1H, s).

DESCRIPTION 23

(3R,4R)-3-{(1R)-1-[3,5-bis(trifluoromethyl)phenyl]ethoxy}-tetrahydro-5-methylene-4-phenylpyran By analogy with Description 21 using Description 20b to afford the title compound as a yellow oil.

¹H NMR (CDCl₃, 360 MHz): δ 1.83 (3H, d, J 6.7 Hz), 3.87 (1H, d, J 10.2 Hz), 3.48 (1H, dd, J 10.9, 9.8 Hz), 3.71 (1H, td, J 9.8, 4.6 Hz), 4.08 (1H, d, J 12.6 Hz), 4.22–4.36 (4H, m), 4.93 (1H, s), 6.98–7.03 (2H, m), 7.08–7.18 (3H, m), 7.23–7.27 (2H, m), 7.65 (1H, s).

DESCRIPTION 24

((3RS,4S,5S)-5-{(1R)-1-[3,5-Bis(trifluoromethyl) phenyl]ethoxy}-tetrahydro-4-phenylpyran-3-yl) methanol To a stirred solution of the product from Description 13 (125 mg) in tetrahydrofuran (5 ml) was added borane-tetrahydrofuran complex (1M solution in tetrahydrofuran, 2.5 ml) at 0° C. After 90 minutes, water (0.5 ml), hydrogen peroxide (30% solution in water, 1.5 ml) and sodium hydroxide (2.5M, 1.5 ml) were added and the mixture stirred for 30 minutes. Sodium sulfite (0.8M, 5 ml) and hydrochloric acid (1M, 2.5 ml) were added and the reaction stirred for 30 minutes before extracting into ethyl acetate. The combined organics were washed with saturated NaHCO₃ solution and dried (brine, MgSO₄) before concentrating under reduced pressure to give a crude oil. This was purified on silica eluting with 30% ethyl acetate/iso-hexane to afford the title compounds as a 3:1 mixture of diastereomers in favour of the (3R) isomer:

Diagnostic signals for (3R,4S,5S) isomer: ¹H NMR (CDCl₃, 400 MHz): δ 1.09 (3H, d, J 6.5 Hz), 4.40 (1H, q, J 6.5 Hz).

Diagnostic signals for (3S,4S,5S) isomer: ¹H NMR (CDCl₃, 400 MHz): δ 0.94 (3H, d, J 6.4 Hz), 3.86 (1H, q, J 6.4 Hz).

DESCRIPTION 25

((3RS,4R,5S)-5-{(1R)-1-[3,5-Bis(trifluoromethyl) phenyl]ethoxy}-tetrahydro-4-phenylpyran-3-yl) methanol By analogy with Description 24 using the product from Description 21 to give a crude oil which was purified on silica eluting with 15–35% ethyl acetate/iso-hexane to afford the title compounds as an 8:1 mixture of diastereomers in favour of the (3S) isomer:

Diagnostic signals for (3S,4R,5S) isomer: ¹H NMR (CDCl₃, 400 MHz): δ 1.38 (3H, d, J 6.7 Hz), 4.65 (1H, q, J 6.7 Hz).

Diagnostic signals for (3R,4R,5S) isomer: ¹H NMR (CDCl₃, 400 MHz): δ 1.55 (3H, d, J 6.7 Hz), 4.93 (1H, q, J 6.7 Hz).

DESCRIPTIONS 26a AND 26b (a) ((3R,4S,5R)-5-{(1R)-1-[3,5-Bis(trifluoromethyl) phenyl]ethoxy}-tetrahydro-4-phenylpyran-3-yl) methanol (b) ((3S,4S,5R)-5-{(1R)-1-[3,5-Bis(trifluoromethyl) phenyl]ethoxy}-tetrahydro-4-phenylpyran-3-yl) methanol By analogy with Description 24 using the product from Description 22 to afford a crude oil which was purified on silica eluting with ethyl acetate/iso-hexane to give the title compounds as two discrete diastereomers:

Description 26a, (3R,4S,5R), less polar: ¹H NMR (CDCl₃, 400 MHz): δ 0.92 (3H, d, J 6.7 Hz), 1.54–1.56 (1H, m), 2.23 (1H, p, J 6.3 Hz), 2.84 (1H, dd, J 7.8, 5.9 Hz), 3.19 (1H, dd, J 10.6, 5.9 Hz), 3.26–3.49 (3H, m), 3.76 (1H, dd, J 12.1, 3.1 Hz), 3.98 (1H, dq, 10.6, 2.7 Hz), 4.93 (1H, q, J 6.3 Hz), 7.00–7.03 (2H, m), 7.20–7.26 (4H, m), 7.83 (1H, s).

Description 26b, (3S,4S,5R), more polar: ¹H NMR (CDCl₃, 400 MHz): δ 1.54 (3H, d, 6.7 Hz), 2.06–2.11 (1H, m), 3.17 (1H, dd, J 5.1, 3.1 Hz), 3.19 (1H, dd, J 12.9, 1.6 Hz), 3.65–3.67 (1H, m), 3.71 (2H, ddd, J 11.7, 7.8, 3.1 Hz), 4.02 (1H, dd, J 11.4, 7.0 Hz), 4.28 (2H, dt, J 12.9, 3.5 Hz), 4.79 (1H, q, 6.3 Hz), 7.22–7.33 (5H, m), 7.61 (2H, s), 7.74 (1H, s).

DESCRIPTION 27

((3RS,4R,5R)-5-{(1R)-1-[3,5-Bis(trifluoromethyl) phenyl]ethoxy}-tetrahydro-4-phenylpyran-3-yl) methanol By analogy with Description 24 using the product from Description 23 to afford the title compounds as a crude 2:1 mixture of diastereomers in favour of the (3S) isomer.

Diagnostic signals for (3S,4R,5R) isomer: ¹H NMR (CDCl₃, 400 MHz): δ 1.35 (3H, d, J 6.7 Hz), 4.49 (1H, q, J 6.7 Hz).

Diagnostic signals for (3R,4R,5R) isomer: ¹H NMR (CDCl₃, 400 MHz): δ 1.30 (3H, d, J 6.7 Hz), 4.76 (1H, q, 6.7 Hz).

DESCRIPTION 28

(3RS,4S,5S)-5-{(1R)-1-[3,5-Bis(trifluoromethyl) phenyl]ethoxy}-tetrahydro-4-phenylpyran-3-carbaldehyde To a stirred solution of oxalyl chloride (18.2 μl) in dichloromethane (5 ml) at −78° C. was added dimethylsulfoxide (23.7 μl) over 5 minutes. After 15 minutes, a solution of the product from Description 24 (75 mg) in dichloromethane (2 ml) was added over 20 minutes and the reaction left for 30 minutes before adding triethylamine (104 μl) over 5 minutes. The mixture was left to warm to ambient temperature over 16 hours and diluted with dichloromethane (10 ml) before washing with saturated NH₄Cl solution. The organics were dried (brine, MgSO₄) and concentrated under reduced pressure to afford a crude oil which was purified on silica eluting with 20% ethyl acetate/iso-hexane to give the title compounds as a 1:1 mixture of diastereomers.

Diagnostic signals for (3R,4S,5S) isomer: ¹H NMR (CDCl₃, 400 MHz): δ 1.19 (3H, d, J 6.5 Hz), 4.50 (1H, q, J 6.5 Hz).

Diagnostic signals for (3S,4S,5S) isomer: ¹H NMR (CDCl₃, 400 MHz): δ 0.98 (3H, d, J 6.4 Hz), 3.85 (1H, q, J 6.4 Hz).

DESCRIPTION 29

(3S,4R,5S)-5-{(1R)-1-[3,5-Bis(trifluoromethyl) phenyl]ethoxy}-tetrahydro-4-phenylpyran-3-carbaldehyde By analogy with Description 28 using the product from Description 25 to afford the title compound as a crude yellow oil.

¹H NMR (CDCl₃, 360 MHz): δ 1.41 (3H, d, J 6.3 Hz), 2.66–2.72 (1H, m), 3.40–3.48 (2H, m), 3.67 (1H, dd, J 11.6, 2.1 Hz), 3.84 (1H, dd, J 12.6, 2.5 Hz), 4.04 (1H, s), 4.52 (1H, dd, J 11.9, 1.8 Hz), 4.58 (1H, q, J 6.3 Hz), 7.16–7.51 (5H, m), 7.74 (2H, s), 7.77 (1H, s), 10.01 (1H, s).

DESCRIPTION 30

(3R,4R,5S)-5-{(1R)-1-[3,5-Bis(trifluoromethyl)phenyl]ethoxy}-tetrahydro-4-phenylpyran-3-carbaldehyde To a stirred solution of the product from Description 29 (320 mg) in dichloromethane (10 ml) was added 1,8-diazabicyclo-[5.4.0]undec-7-ene (1 drop) and the mixture left for 1 hour. The reaction was concentrated under reduced pressure to afford the title compound as a crude yellow oil.

$^1$H NMR (CDCl$_3$, 360 MHz): δ 1.13 (3H, d, J 6.3 Hz), 3.17 (1H, dd, J 12.3, 2.8 Hz), 3.31–3.51 (3H, m), 3.67–3.78 (2H, m), 3.92 (1H, q, J 6.3 Hz), 4.29 (1H, dd, J 7.0, 4.6 Hz), 7.25–7.45 (5H, m), 7.69 (2H, s), 7.76 (1H, s), 9.58 (1H, d, J 1.8 Hz).

DESCRIPTION 31

(3R,4S,5R)-5-{(1R)-1-[3,5-Bis(trifluoromethyl)phenyl]ethoxy}-tetrahydro-4-phenylpyran-3-carbaldehyde To a stirred solution of the product from Description 26b (100 mg) in dichloromethane (5 ml) was added Dess-Martin periodinane (95 mg) and the mixture left for 10 minutes. The reaction was quenched with sodium thiosulfate (300 mg) in saturated NaHCO$_3$ solution (1.5 ml) and left to stir for 15 minutes before extracting into dichloromethane (×3). The combined organics were dried (brine, MgSO$_4$) and concentrated under reduced pressure to give a crude oil which was purified on silica eluting with 15–30% ethyl acetate/iso-hexane to afford the title compound as a yellow oil.

$^1$H NMR (CDCl$_3$, 400 MHz): δ 1.45 (3H, d, J 6.3 Hz), 2.68–2.73 (1H, m), 3.36 (1H, dd, J 4.2, 1.8 Hz), 3.48 (1H, d, J 13.0 Hz), 3.69 (1H, ddd, J 11.6, 1.8, 1.1 Hz), 3.79 (1H, s), 4.33 (1H, dd, J 13.0, 1.4 Hz), 4.59 (1H, d, J 11.6 Hz), 4.79 (1H, q, J 6.3 Hz), 7.23–7.33 (5H, m), 7.58 (2H, s), 7.76 (1H, s), 10.08 (1×, s).

DESCRIPTION 32

(3S,4S,5R)-5-{(1R)-1-[3,5-Bis(trifluoromethyl)phenyl]ethoxy}-tetrahydro-4-phenylpyran-3-carbaldehyde By analogy with Description 30 using the product from Description 31 to afford the title compound as a crude oil which was purified on silica, eluting with dichloromethane, to give the title compound as a yellow oil.

Diagnostic signals $^1$H NMR (CDCl$_3$, 400 MHz): δ 1.42 (3H, d, J 6.3 Hz), 4.45 (1H, q, J 6.3 Hz), 9.51 (1H, d, J 2.0 Hz).

DESCRIPTION 33

(3RS,4R,5R)-5-{(1R)-1-[3,5-Bis(trifluoromethyl)phenyl]ethoxy}-tetrahydro-4-phenylpyran-3-carbaldehyde By analogy with Description 31 using the product from Description 27 to afford the title compounds as a crude oil which was purified on silica eluting with 15–30% ethyl acetate/iso-hexane to afford the title compounds as a 3:1 mixture of diastereomers in favour of the (3S) isomer.

Signals for (3S,4R,5R) isomer: $^1$H NMR (CDCl$_3$, 400 MHz): δ 1.39 (3H, d, J 6.7 Hz), 2.83–2.88 (1H, m), 3.16 (1H, dd, J 10.2, 4.9 Hz), 3.38 (1H, dd, J 11.2, 9.1 Hz), 3.70 (1H, dd, J 11.9, 3.2 Hz), 4.12–4.30 (2H, m), 4.33 (1H, dd, J 11.2, 4.6 Hz), 4.57 (1H, q, J 6.7 Hz), 7.00–7.22 (5H, m), 7.38 (2H, s), 7.71 (1H, s), 9.72 (1H, d, J 2.1 Hz).

Signals for (3R,4R,5R) isomer: $^1$H NMR (CDCl$_3$, 400 MHz): δ 1.31 (3H, d, J 6.3 Hz), 2.89–3.05 (2H, m), 3.30 (1H, t, J 10.2 Hz), 3.48 (1H, t, J 11.6 Hz), 3.59 (1H, td, J 9.82, 4.6 Hz), 4.12–4.30 (3H, m), 7.00–7.22 (5H, m), 7.35 (1H, s), 7.65 (2H, s), 9.31 (1H, d, J 1.4 Hz).

DESCRIPTION 34

(3R)-1-((3RS,4S,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid ethyl ester To a stirred solution of the product of Description 28 (50 mg) in 1,2-ichloroethane was added the half di-p-toluoyl-D-tartrate salt of (R)-3-methylpiperidine-3-carboxylic acid ethyl ester (81.5 mg), triethylamine (31 µl) and sodium triacetoxyborohydride (47.5 mg). After 16 hours, the reaction was quenched with saturated NaHCO$_3$ solution and extracted into dichloromethane (×3). The combined organics were dried (brine, MgSO$_4$) and concentrated under reduced pressure to give a crude oil which was purified on silica eluting with 20% ethyl acetate/iso-hexane to afford the title compounds as a 1:1 mixture of diastereomers.

Signals for mixture: $^1$H NMR (CDCl$_3$, 400 MHz): δ 0.93 (3H, d, J 6.4 Hz), 1.07 (6H, s), 1.21–1.27 (9H, m), 1.47–1.53 (5H, m), 1.82–2.08 (7H, m), 2.20–2.41 (6H, m), 2.98–3.10 (3H, m), 3.10–3.20 (3H, m), 3.35–3.43 (2H, m), 3.70–3.79 (3H, m), 3.81–3.90 (1H, m), 4.03–4.21 (10H, m), 4.59 (1H, q, J 6.5 Hz), 7.22–7.41 (10H, m), 7.52 (2H, s), 7.70 (2H, s), 7.74–7.75 (2H, m).

MS (ES+) m/z 602 (M+1, 100%).

DESCRIPTION 35

(3R)-1-((3S,4R,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid ethyl ester By analogy with Description 34 using the product from Description 29 to give a crude oil which was purified on silica eluting with 15–20% ethyl acetate/iso-hexane to afford the title compound as a yellow oil.

$^1$H NMR (CDCl$_3$, 400 MHz): δ 1.08 (3H, s), 1.28 (3H, t, J 7.04 Hz), 1.32 (3H, d, J 6.7 Hz), 1.46–1.69 (4H, m), 1.96–2.12 (3H, m), 2.14–2.22 (1H, m), 2.35–2.45 (1H, m), 2.48–2.57 (1H, m), 2.86–2.95 (1H, m), 3.28–3.33 (1H, m), 3.47–3.53 (1H, m), 3.64 (1H, dd, J 11.3, 3.5 Hz), 3.85–3.91 (2H, m), 3.99–4.20 (3H, m), 4.66 (1H, q, J 6.3 Hz), 7.27–7.31 (1H, m), 7.31–7.38 (2H, m), 7.49–7.54 (2H, m), 7.77 (1H, s), 7.79 (2H, s).

MS (ES+) m/z 602 (M+1, 100%).

DESCRIPTION 36

(3R)-1-((3R,4R,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid ethyl ester By analogy with Description 34 using the product from Description 30 to give a crude oil which was purified on silica eluting with 10–15% ethyl acetate/iso-hexane to afford the title compound as a yellow oil.

$^1$H NMR (CDCl$_3$, 360 MHz): δ 1.09 (3H, s), 1.13 (3H, d, J 6.7 Hz), 1.26 (3H, t, J 7.01 Hz), 1.51–1.66 (3H, m), 1.81–2.06 (4H, m), 2.10 (1H, dd, J 13.0, 3.2 Hz), 2.54 (1H, dd, J 11.9, 2.5 Hz), 2.60–2.71 (2H, m), 2.73–2.84 (1H, m), 3.10 (1H, t, J 11.6 Hz), 3.31 (1H, s), 3.56 (1H, d, J 11.9 Hz), 3.69 (1H, d, J 12.3 Hz), 3.75 (1H, q, J 6.3 Hz), 4.08–4.20 (2H, m), 4.33 (1H, dd, J 11.6, 4.6 Hz), 7.28–7.42 (5H, m), 7.68 (2H, s), 7.74 (1H, s).

MS (ES+) m/z 602 (M+1, 100%).

DESCRIPTION 37

(3R)-1-((3R,4S,5R)-{(1R)-1-[3,5-Bis(trifluoromethyl)phenyl]ethoxy}-tetrahydro-4-phenylpyran-3-ylmethyl)-3-methylpiperidine-3-carboxylic acid ethyl ester By analogy with Description 34 using the product from Description 31 to afford the title compound as a crude yellow oil.

$^1$H NMR (CDCl$_3$, 400 MHz): δ 1.11 (3H, s), 1.25 (3H, t, J 7.1 Hz), 1.45 (3×, d, J 6.7 Hz), 1.98–2.05 (2H, m), 2.13–2.21 (2H, m), 2.27–2.38 (2H, m), 2.48 (1H, d, J 12.9 Hz), 2.60–2.74 (1H, m), 2.82–2.93 (1H, m), 2.98–3.05 (1H, m), 3.28 (1H, t, J 4.7 Hz), 3.36 (1H, dd, J 12.5, 1.6 Hz), 3.61 (1H, dd, J 11.4, 3.5 Hz), 3.69 (1H, dd, J 12.1, 3.5 Hz), 3.81–3.87 (1H, m), 3.95 (1H, dd, J 11.4, 7.0 Hz), 4.04–4.24 (4H, m), 4.72 (1H, q, J 6.7 Hz), 7.16–7.20 (3H, m), 7.27–7.30 (2H, m), 7.53 (2H, s), 7.71 (1H, s).

MS (ES+) m/z 602 (M+1, 100%).

DESCRIPTION 38

(3R)-1-((3S,4S,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid ethyl ester By analogy with Description 34 using the product from Description 32 to give a crude oil which was purified on silica eluting with 10–33% ethyl acetate/iso-hexane to afford the title compound as a yellow oil.

$^1$H NMR (CDCl$_3$, 360 MHz): δ 1.14 (3H, s), 1.16–1.29 (2H, m), 1.33 (3H, t, J 7.0 Hz), 1.41 (3H, d, J 6.3 Hz), 1.44–1.53 (2H, m), 1.61–1.71 (1H, m), 1.79–1.86 (1H, m), 1.96–2.08 (3H, m), 2.22–2.30 (1H, m), 2.43–2.48 (1H, m), 3.06–3.16 (2H, m), 3.21 (1H, s), 3.40 (1H, d, J 12.3 Hz), 4.10–4.23 (3H, m), 4.84–4.44 (2H, m), 7.14–7.30 (7H, m), 7.62 (1H, s).

MS (ES+) m/z 603 (M+2, 100%).

DESCRIPTION 39

(3R)-1-((3R,4R,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid ethyl ester To a stirred solution of the product from Description 33 (20 mg) in chloroform-d (2 ml) was added 1,8-diazabicyclo[5.4.0]undec-7-ene (1 drop) and the mixture heated to reflux. The reaction was allowed to cool to ambient temperature and then concentrated under reduced pressure before proceeding by analogy with Description 34 to afford the title compound as a crude yellow oil.

$^1$H NMR (CDCl$_3$, 400 MHz): δ 1.05 (3H, s), 1.12–1.29 (6H, m), 1.79 (1H, dd, J 13.0, 3.5 Hz), 1.84–2.34 (3H, m), 2.37–2.52 (2H, m), 2.56–2.74 (2H, m), 2.94–3.13 (2H, m), 3.25 (1H, t, J 10.5 Hz), 3.33 (1H, d, J 12.6 Hz), 3.44–3.59 (2H, m), 4.08–4.23 (6H, m), 6.94–6.98 (2H, m), 7.06–7.15 (3H, m), 7.18 (2H, s), 7.63 (1H, s).

MS (ES+) m/z 602 (M+1, 100%).

DESCRIPTION 40

4-[2-(tert-Butyldimethylsilyloxymethyl)-3-phenylallyl]-morpholine

Methanesulphonyl chloride (38 ml, 490 mmol) was added dropwise to a stirred solution of the product from Description 4 (90.00 g, 323 mmol), 4-(dimethylamino)pyridine (1.1 g, 9 mmol) and triethylamine (70 ml) in dichloromethane (550 ml) over 45 min. at +5° C.→+15° C. After stirring at +10° C. for 1 hour the reaction was treated triethylamine (70 ml) and morpholine (100 ml). The mixture was stirred for 3 hours and left overnight at room temperature. Water was added and the mixture was extracted with dichloromethane. The combined organic extracts were washed with saturated aqueous NaHCO$_3$, dried (Na$_2$SO$_4$) and concentrated in vacuo. The residue was purified by chromatography on silica to give the title compound (90 g, 80%).

$^1$H NMR (CDCl$_3$, 360 MHz): δ 0.06 (6H, s), 0.91 (9H, s), 2.46 (4H, m), 2.51 (1H, m), 3.12 (2H, d, J 1.1 Hz), 3.71 (4H, t, J 4.6 Hz), 4.28 (2H, s), 6.57 (1H, s), 7.19–7.36 (5H, m).

DESCRIPTION 41

{(1R)-1-[3,5-Bis(trifluoromethyl)phenyl]ethoxy}acetic acid chloride

To a stirred solution of the product from Description 8 (97 g) in dichloromethane (1 L) at −10° C., was added oxalyl chloride (80 ml) dropwise. N,N-Dimethylformamide (2 drops) was then added and the mixture stirred for 12 hours. The reaction mixture was concentrated under reduced pressure and azeotroped with toluene to afford the title compound as a crude black oil.

$^1$H NMR (CDCl$_3$, 360 MHz): δ 1.56 (3H, d, J 6.5 Hz), 4.25 (1H, d, J 18.3 Hz), 4.45 (1H, d, J 18.3 Hz), 4.72 (1H, q, J 6.5 Hz), 7.78 (2H, a), 7.84 (1H, s).

DESCRIPTION 42

4-{(2R,3S)-2-{(1R)-1-[3,5-Bis(trifluoromethyl)phenyl]ethoxy}-4-(tert-butyldimethylsilyloxymethyl)-3-phenylpent-4-enoyl}-morpholine Titanium(IV) chloride tetrahydrofuran complex (1:2, 25 mg, 0.075 mmol) was added dropwise to a stirred at −5° C. solution of the product from Description 40 (150 mg, 0.43 mmol), the product from Description 41 (250 g, 0.75 mmol) and N,N-diisopropylethylamine (0.2 ml) in dichloromethane (1 ml). After stirring for 30 minutes the reaction was quenched with 1M aqueous NaOH (10 ml) and extracted with dichloromethane. The combined organic extracts dried (Na$_2$SO$_4$) and concentrated in vacuo to give a mixture of four diastereoisomers in ratio (2S,3R):(2S,3S):(2R,3S):(2R,3R)=3:1:4.2:1. Diastereoisomers were separated by chromatography on silica (i-hexane:diethyl ether).

4-{(2S,3R)-2-{(1R)-1-[3,5-Bis(trifluoromethyl)phenyl]ethoxy}-4-(tert-butyldimethylsilyloxymethyl)-3-phenylpent-4-enoyl}-morpholine $^1$H NMR (CDCl$_3$, 360 MHz): δ −0.04 (3H, s), −0.03 (3H, s), 0.86 (9H, s), 1.13 (3H, d, J 6.3 Hz), 3.13–3.66 (8H, m), 3.83 (2H, d, J 9.8 Hz), 3.97 (2H, s), 4.35 (1H, q, J 6.3 Hz), 4.70 (1H, d, J 9.8 Hz), 5.12 (1H, s), 5.26 (1H, s), 7.20–7.35 (5H, m), 7.60 (2H, s), 7.74 (1H, s).

4-{(2S,3S)-2-{(1R)-1-[3,5-Bis(trifluoromethyl) phenyl]ethoxy}-4-(tert-butyldimethylsilyloxymethyl)-3-phenylpent-4-enoyl}-morpholine $^1$H NMR (CDCl$_3$, 360 MHz): δ 0.00 (6H, s), 0.88 (9H, s), 1.48 (3H, d, J 6.3 Hz), 2.47 (1H, m), 2.74 (3H, m), 3.01 (2H, m), 3.25 (2H, m), 3.75 (1H, d, J 10.2 Hz), 3.94 (1H, d, J 14.7 Hz), 4.09 (1H, d, J 14.7 Hz), 4.61 (1H, q, J 6.3 Hz), 4.64 (1H, d, J 10.2 Hz), 5.22 (1H, s), 5.50 (1H, s), 7.18–7.29 (5H, m), 7.77 (1H, s), 7.80 (2H, s).

4-{(2R,3S)-2-{(1R)-1-[3,5-Bis(trifluoromethyl) phenyl]ethoxy}-4-(tert-butyldimethylsilyloxymethyl)-3-phenylpent-4-enoyl}-morpholine $^1$H NMR (CDCl$_3$, 360 MHz): δ −0.08 (6H, s), 0.82 (9H, s), 1.34 (3H, d, J 6.3 Hz), 3.43–3.79 (8H, m), 3.83 (1H, d, J 10.2 Hz), 3.88 (2H, s), 4.48 (1H, d, J 10.2 Hz), 4.49 (1H, q, J 6.3 Hz), 5.02 (1H, s), 5.18 (1H, s), 7.12–7.28 (5H, m), 7.36 (2H, s), 7.74 (1H, s).

4-{(2R,3R)-2-{(1R)-1-[3,5-Bis(trifluoromethyl) phenyl]ethoxy}-4-(tert-butyldimethylsilyloxymethyl)-3-phenylpent-4-enoyl}-morpholine $^1$H NMR (CDCl$_3$, 360 MHz): δ −0.00 (6H, s), 0.88 (9H, s), 1.48 (3H, d, J 6.3 Hz), 2.77 (2H, m), 3.02 (1H, m), 3.11–3.37 (4H, m), 3.40–3.56 (4H, m), 3.45 (1H, d, J 13.3 Hz), 3.71 (1H, d, J 10.2 Hz), 3.92 (1H, d, J 14.7 Hz), 4.09 (1H, d, J 14.7 Hz), 4.38 (1H, d, J 10.2 Hz), 4.48 (1H, q, J 6.3 Hz), 4.75 (1H, s), 5.38 (1H, s), 7.19 (5H, m), 7.74 (2H, s), 7.84 (1H, s).

DESCRIPTION 43

(3R,4S)-3-{(1R)-1-[3,5-Bis(trifluoromethyl)phenyl] ethoxy}-5-methylene-4-phenyl-tetrahydropyran-2-one A mixture of the product from Description 42 (11 g, 17 mmol), ethereal HCl (1M, 45 ml) and ethanol (100 ml) was stirred at reflux for 2 hours, then concentrated in vacuo. Toluene (200 ml) was added and the mixture was subjected for azeotropic distillation over 7 hours, then concentrated in vacuo and purified by chromatography on silica (i-hexane:diethyl ether) to give the title compound (6.1 g, 80%).

$^1$H NMR (CDCl$_3$, 360 MHz): δ 1.47 (3H, d, J 6.3 Hz), 3.83 (1H, dm, J 10.5 Hz), 4.04 (1H, d, J 10.2 Hz), 4.83 (1H, d, J 13.0 Hz), 4.85 (2H, s), 4.90 (1H, s), 4.92 (1H, d, J 13.3 Hz), 4.93 (1H, q, J 6.3 Hz), 5.27 (1H, s), 7.02 (2H, m) 7.17–7.27 (3H, m), 7.27 (2H, s), 7.68 (1H, s).

DESCRIPTION 44

(3R,4S)-3-{(1R)-1-[3,5-Bis(trifluoromethyl)phenyl] ethoxy}-5-methylene-4-phenyl-tetrahydropyran A solution of diisobutylaluminium hydride in dichloromethane (1M, 22 ml) was added dropwise to a stirred solution of the product from Description 43 (7.2 g, 16.2 mmol) in dichloromethane (70 ml) at −78° C. The mixture was stirred for 45 minutes and ethyl acetate (2 ml) was added followed by dichloromethane (150 ml) and water (2 ml, dropwise). The mixture was stirred at room temperature for 1 hour, (Na$_2$SO$_4$) and concentrated in vacuo to give a 1.6:1 mixture of diastereoisomeric lactols.

The crude mixture of lactols was treated with dichloromethane (70 ml), triethylsilane (7 ml, 44 mmol) and cooled to 0° C. Boron trifluoride diethyl etherate (2.5 ml, 19.7 mmol) was added and the mixture was stirred for 2 hours, then quenched with saturated aqueous NaHCO$_3$ and dichloromethane was removed in vacuo. The residue was extracted with i-hexane. The combined organic extracts were dried (Na$_2$SO$_4$) and concentrated in vacuo. The residue was purified by chromatography on silica (i-hexane:diethyl ether) to give the title compound (5.8 g, 83%).

$^1$H NMR (CDCl$_3$, 360 MHz): δ 1.33 (3H, d, J 6.7 Hz), 3.37 (1H, d, J 10.2 Hz), 3.48 (1H, dd, J 10.9, 9.8 Hz), 3.72 (1H, dt, J 10.2, 4.9 Hz), 4.03 (1H, d, J 12.6 Hz), 4.26 (1H, d, J 12.6 Hz), 4.25–4.36 (3H, m), 4.93 (1H, s), 7.01 (2H, m) 7.16 (3H, m), 7.25 (2H, s), 7.65 (1H, s).

DESCRIPTION 45

[(3RS,4R,5R)-5-{(1R)-1-[3,5-Bis(trifluoromethyl) phenyl]ethoxy}-4-phenyl-tetrahydropyran-3-yl] methanol A solution of borane-tetrahydrofuran complex in tetrahydrofuran (1M, 25 ml) was added dropwise to a stirred, ice-bath cooled solution of the product from Description 44 (5.8 g, 13.5 mmol) in tetrahydrofuran (70 ml). The cold-bath was removed and the mixture was stirred at ambient temperature. After 30 minutes, the mixture was cooled to 0° C. and carefully treated with 2M aqueous NaOH (20 ml) and 35% hydrogen peroxide (20 ml). The cold bath was removed and the mixture was stirred for 1 hour. After cooling to 0°, the reaction was carefully treated with 25% aqueous solution of Na$_2$S$_3$O$_5$ (125 ml) and extracted into ethyl acetate. The combined organic extracts were dried (Na$_2$SO$_4$) and concentrated in vacuo. The residue was purified by chromatography on silica (i-hexane:ethyl acetate) to give a mixture of diastereoisomeric alcohols (5.34 g) in the ratio (3S):(3R)= 1.9:1.

DESCRIPTION 46

[(3S,4R,5R)-5-{(1R)-1-[3,5-Bis(trifluoromethyl) phenyl]ethoxy}-4-phenyl-tetrahydropyran]-3-carbaldehyde Dimethyl sulphoxide (3 ml, 42 mmol) was added dropwise to a stirred solution of oxalyl chloride (1.7 ml, 19.5 mmol) in dichloromethane (30 ml) at −60° C. After 10 minutes, a solution of product from Description 45 (5.34 g) in dichloromethane (25 ml) was added dropwise. The mixture was stirred for 30 minutes at −60° C. and triethylamine (8 ml) was added dropwise. The mixture was warm up to 0° C. over 30 minutes, then quenched with water and extracted into a mixture i-hexane:diethyl ether (1:1). The combined organic extracts were washed with water (4×), brine, dried (Na$_2$SO$_4$) and concentrated in vacuo. The residue treated with dichloromethane (30 ml) followed by DBU (0.2 ml) and stirred overnight at room temperature. Dichloromethane was removed in vacuo and the residue was purified by chromatography on silica (i-hexane:ethyl acetate) to give the title compound (4.0 g, 66% two steps).

$^1$H NMR (CDCl$_3$, 360 MHz): δ 1.32 (3H, d, J 6.3 Hz), 2.90 (1H, dd, J 11.9, 9.5 Hz), 3.30 (1H, dddd, J 12.3, 10.5, 4.6, 1.4 Hz), 3.30 (1H, dd, J 11.2, 10.2 Hz), 3.48 (1H, dd, J 11.6, 10.5 Hz), 3.59 (1H, dt, J 9.8, 4.6 Hz), 4.15 (1H, dd, J 11.9, 4.6 Hz), 4.20–4.29 (3H, m), 7.08 (2H, m) 7.17 (3H, m), 7.20 (2H, s), 7.65 (1H, s).

DESCRIPTION 47

[(3R,4R,5R)-5-{(1R)-1-[3,5-Bis(trifluoromethyl) phenyl]ethoxy}-4-phenyl-tetrahydropyran-3-yl] methanol Sodium borohydride (280 mg, 7.4 mmol) was added to a stirred, ice-bath cooled solution of product from Description 46 (2.86 g, 6.4 mmol) in methanol (30 ml). The mixture was stirred for 30 minutes and quenched with saturated aqueous $NaHCO_3$ (20 ml) and water (100 ml) and extracted into dichloromethane. The combined organic extracts were dried ($Na_2SO_4$) and concentrated in vacuo to give the title compound (3 g).

$^1$H NMR ($CDCl_3$, 360 MHz): δ 1.30 (3H, d, J 6.3 Hz), 2.07 (1H, m), 2.55 (1H, dd, J 11.9, 10.2 Hz), 3.22 (1H, m), 3.29 (1H, t, J 10.2 Hz), 3.34 (1H, m), 3.37 (1H, t, J 11.2 Hz), 3.57 (1H, dt, J 9.8, 4.6 Hz), 4.15 (1H, dd, J 11.9, 4.6 Hz), 4.19–4.28 (3H, m), 7.02 (2H, m) 7.14 (3H, m), 7.19 (2H, s), 7.64. (1H, s).

DESCRIPTION 48

Methanesulphonic acid [(3S,4R,5R)-5-{(1R)-1-[3,5-bis(trifluoromethyl)phenyl]ethoxy}-4-phenyl-tetrahydropyran-3-yl]methyl ester Methanesulphonyl chloride (0.75 ml, 9.7 mmol) was added to a stirred, ice-bath cooled solution of product from Description 47 (3.0 g), triethylamine (1.7 ml, 12.1 mmol), N,N-dimethylaminopyridine (82 mg, 0.66 mmol) in dichloromethane (15 ml). The cold-bath was removed and the mixture was stirred at ambient temperature. After 20 minutes, the mixture was quenched with saturated aqueous $NaHCO_3$ (20 ml) and water (100 ml) and extracted into dichloromethane. The combined organic extracts were dried ($Na_2SO_4$) and concentrated in vacuo to give the title compound (3.62 g).

$^1$H NMR ($CDCl_3$, 360 MHz): δ 1.30 (3H, d, J 6.6 Hz), 2.28 (1H, m), 2.58 (1H, dd, J 11.9, 10.2 Hz), 2.82 (3H, s), 3.30 (1H, t, J 10.2 Hz), 3.39 (1H, t, J 11.2 Hz), 3.56 (1H, dt, J 9.8, 4.6 Hz), 3.74 (1H, dd, J 10.2, 6.7 Hz), 3.88 (1H, dd, J 10.2, 3.2 Hz), 4.12 (1H, dd, J 11.3, 4.6 Hz), 4.24 (1H, q, J 6.3 Hz), 4.25 (1H, dd, J 11.2, 4.9 Hz), 7.01 (2H, m) 7.17 (3H, m), 7.18 (2H, s), 7.64 (1H, s).

DESCRIPTION 49

[(3S,4R,5R)-5-{(1R)-1-[3,5-Bis(trifluoromethyl) phenyl]ethoxy}-4-phenyl-tetrahydro-pyran-3-yl] methyl-2H-tetrazole A mixture of the product from Example 7 (300 mg, 0.66 mmol), sodium azide (195 mg, 3.0 mmol), triethylamine hydrochloride (485 mg) and N,N-dimethylformamide (2.5 ml) was stirred at +130° C. overnight, then cooled to room temperature and diluted with ethyl acetate (70 ml). The organic phase were washed with water (4×), dried ($Na_2SO_4$) and concentrated in vacuo. The residue was purified by chromatography on silica to give the title compound (170 mg, 51%).

$^1$H NMR ($CDCl_3$, 400 MHz): δ 1.29 (3H, d, J 6.3 Hz), 2.48 (2H, m), 1.93 (1H, dd, J 15.3, 8.2 Hz), 2.64 (1H, dd, J 15.3, 3.9 Hz), 3.29 (1H, t, J 11.4 Hz), 3.30 (1H, t, J 11.0 Hz), 3.57 (1H, dt, J 9.8, 4.7 Hz), 3.93 (1H, dd, J 11.7, 3.9 Hz), 4.20 (1H, q, J 6.7 Hz), 4.23 (1H, dd, J 11.0, 5.1 Hz), 7.01 (2H, m) 7.07 (3H, m), 7.17 (2H, s), 7.63 (1H, s).

DESCRIPTION 50

[(3S,4R,5R)-5-{(1R)-1-[3,5-bis(trifluoromethyl) phenyl]ethoxy}-4-phenyl-tetrahydro-pyran-3-carboxylic acid A mixture of the product from Example 7 (225 mg, 0.49 mmol), 6M hydrochloric acid (5 ml) and acetic acid (5 ml) was stirred at +100° C. for 42 hours, then cooled to room temperature and diluted with ethyl acetate. The mixture was washed with water. The organic phase were washed with water, dried ($Na_2SO_4$) and concentrated in vacuo to give the title compound (163 mg, 72%).

$^1$H NMR ($CDCl_3$, 360 MHz): δ 1.29 (3H, d, J 6.7 Hz), 1.87 (1H, dd, J 16.5, 9.1 Hz), 2.08 (1H, dd, J 16.5, 3.2 Hz), 2.26–2.46 (2H, m), 3.17 (1H, t, J 10.9 Hz), 3.28 (1H, t, J 10.5 Hz), 3.56 (1H, dt, J 9.8, 4.9 Hz), 4.08 (1H, dd, J 11.2, 3.9 Hz), 4.20 (1H, q, J 6.3 Hz), 4.24 (1H, dd, J 11.2, 4.9 Hz), 6.99 (2H, m) 7.13 (3H, m), 7.18 (2H, s), 7.64 (1H, s).

EXAMPLES 1a AND 1b (a) (3R)-1-((3R,4S,5S)-5-{(1R)-1-[3,5-Bis (trifluoromethyl)phenyl]-ethoxy}-tetrahydro-4-phenylpyran-3-ylmethyl)-3-methylpiperidine-3-carboxylic acid (b) (3R)-1-((3S,4S,5S)-5-{(1R)-1-[3,5-Bis (trifluoromethyl)phenyl]ethoxy}-tetrahydro-4-phenylpyran-3-ylmethyl)-3-methylpiperidine-3-carboxylic acid To a stirred solution of the product from Description 34 (60 mg) in methanol (1 ml) was added sodium hydroxide (1M, 0.5 ml) and the mixture heated to 65° C. After 30 hours, the reaction was concentrated under reduced pressure and taken up in water/ethyl acetate. The aqueous phase was adjusted to pH≈7 by the addition of hydrochloric acid (2M) and the mixture extracted into further ethyl acetate (×3). The combined organics were dried (brine, $MgSO_4$) and concentrated under reduced pressure to give a crude oil. This was purified on silica eluting with 10% methanol/dichloromethane and freeze dried to afford the title compounds as discrete white solids.

Example 1a, (3R,4S,5S), less polar: $^1$H NMR ($CDCl_3$, 400 MHz): δ 1.10 (3H, s), 1.13 (3H, d, J 6.6 Hz), 1.48–1.69 (4H, m), 1.86 (1H, d, J 14.4 Hz), 2.02 (1H, d, J 11.7 Hz), 2.20–2.23 (2H, m), 2.61–2.63 (1H, m), 2.69 (1H, dd, J 13.4, 10.4 Hz), 2.82 (1H, d, J 11.7 Hz), 3.15 (1H, dd, J 11.2, 9.0 Hz), 3.22 (1H, dd, J 10.0, 4.6 Hz), 3.58 (1H, d, J 11.2 Hz), 3.78 (1H, dd, J 11.2, 4.6 Hz), 3.85–3.92 (1H, m), 4.59 (1H, q, J 6.6 Hz), 7.24–7.31 (3H, m), 7.37–7.41 (2H, m), 7.68 (2H, s), 7.77 (1H, s).

MS (ES+) m/z 574 (M+1, 100%).

Example 1b, (3S,4S,5S), more polar: $^1$H NMR ($CDCl_3$, 400 MHz): δ 0.93 (3H, d, J 6.4 Hz), 1.10 (3H, s), 1.48–1.62 (3H, m), 1.73–1.82 (1H, m), 1.87 (1H, d, J 15.2 Hz), 2.01 (1H, td, J 12.6, 3.5 Hz), 2.13–2.16 (1H, m), 2.21–2.27 (1H, m), 2.40 (1H, t, J 11.0 Hz), 2.76 (1H, d, J 11.7 Hz), 3.13–3.19 (2H, m), 3.44 (1H, td, J 10.0, 5.0 Hz), 3.75 (1H, dd, J 11.1, 5.0 Hz), 3.84 (1H, q, J 6.4 Hz), 4.16 (1H, dd, J 11.3, 3.9 Hz), 7.26–7.44 (5H, m), 7.51 (2H, s), 7.75 (1H, s).

MS (ES+) m/z 574 (M+1, 100%).

EXAMPLE 2

(3R)-1-((3S,4R,5S)-5-{(1R)-1-[3,5-Bis (trifluoromethyl)phenyl]ethoxy}-tetrahydro-4-phenylpyran-3-ylmethyl)-3-methylpiperidine-3-carboxylic acid By analogy with Example 1 using the product from Description 35 to afford a crude oil. This was purified by LOBAR® eluting with 10% methanol/dichloromethane to afford the title compound as a white crystalline solid.

$^1$H NMR (CDCl$_3$, 400 MHz): δ 1.05 (3H, s), 1.50 (3H, d, J 6.3 Hz), 1.59–1.71 (2H, m), 1.79–1.94 (3H, m), 2.10–2.25 (2H, m), 2.46 (1H, dd, J 12.9, 0.8 Hz), 2.65 (1H, d, J 11.4 Hz), 2.97 (1H, d, J 12.5 Hz), 3.07 (1H, dd, J 13.7, 9.8 Hz), 3.27 (1H, t, J 4.3 Hz), 3.42 (1H, dd, J 12.5, 1.2 Hz), 3.70 (1H, dd, J 11.7, 1.2 Hz), 3.97 (1H, dd, J 12.5, 3.1 Hz), 4.01 (1H, d, J 1.2 Hz), 4.08 (1H, dd, J 12.9, 2.4 Hz), 4.75 (1H, q, J 6.3 Hz), 7.28–7.33 (1H, m), 7.35–7.40 (2H, m), 7.53 (2H, d, J 7.4 Hz), 7.80 (1H, s), 7.85 (2H, s).

MS (ES+) m/z 574 (M+1, 100%).

EXAMPLE 3

(3R)-1-((3R,4R,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid By analogy with Example 1 using the product from Description 36 to afford a crude oil. This was purified by LOBAR® eluting with 10% methanol/dichloromethane to afford the title compound as a white foam.

$^1$H NMR (CDCl$_3$, 400 MHz): δ 1.10 (3H, s), 1.15 (3H, d, J 6.7 Hz), 1.17–1.21 (1H, m), 1.67–1.88 (3H, m), 1.93 (1H, d, J 14.1 Hz), 1.98 (1H, d, J 11.7 Hz), 2.13 (1H, t, J 10.2 Hz), 2.31 (1H, dd, J 12.9, 2.3 Hz), 2.59 (1H, dd, J 11.7, 2.0 Hz), 2.69 (1H, d, J 11.0 Hz), 2.85–2.99 (1H, m), 3.23 (1H, t, J 11.4 Hz), 3.27 (1H, s), 3.36–3.43 (2H, m), 3.73 (1H, d, J 11.7 Hz), 3.89 (1H, q, J 6.3 Hz), 4.29 (1H, dd, J 11.4, 3.9 Hz), 7.31–7.37 (3H, m), 7.38–7.44 (2H, m), 7.70 (2H, s), 7.76 (1H, s).

MS (ES+) m/z 574 (M+1, 100%).

EXAMPLE 4

(3R)-1-((3R,4S,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid By analogy with Example 1 using the product from Description 37 to afford a crude oil. This was purified by LOBAR® eluting with 10% methanol/dichloromethane to afford the title compound as a white foam.

$^1$H NMR (CDCl$_3$, 400 MHz): δ 1.08 (3H, s), 1.45 (3H, d, J 6.3 Hz), 1.48–1.60 (2H, m), 1.62–1.77 (2H, m), 1.85 (1H, d, J 13.0 Hz), 2.06 (1H, d, J 11.6 Hz), 2.16 (1H, s), 2.38 (1H, d, J 11.9 Hz), 2.74 (1H, d, J 6.7 Hz), 2.89 (1H, d, J 11.2 Hz), 2.98 (1H, dd, J 9.8, 13.0 Hz), 3.13 (1H, t, J 3.9 Hz), 3.48 (1H, dd, J 12.6, 1.4 Hz), 3.63 (1H, dd, J 11.9, 1.8 Hz), 3.72 (1H, d, J 1.4 Hz), 4.02 (1H, dd, J 11.9, 3.2 Hz), 4.17 (1H, dd, J 12.3, 3.9 Hz), 4.71 (1H, q, J 6.3 Hz), 7.13–7.24 (5H, m), 7.59 (2H, s), 7.69 (1H, s).

MS (ES+) m/z 574 (M+1, 100%).

EXAMPLE 5

(3R)-1-((3S,4S,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid By analogy with Example 1 using the product from Description 38 to afford a crude oil. This was purified by LOBAR® eluting with 10% methanol/dichloromethane and then by preparative thin layer chromatography eluting with 7.5% methanol/dichloromethane to afford the title compound as a white foam.

$^1$H NMR (CDCl$_3$, 400 MHz): δ 1.18 (3H, s), 1.39–1.46 (1H, m), 1.45 (3H, d, J 6.3 Hz), 1.55–1.64 (1H, m), 1.76 (1H, d, J 11.6 Hz), 1.79–1.88 (1H, m), 1.88–1.96 (1H, m), 2.00 (1H, dd, J 11.2, 3.5 Hz), 2.03–2.07 (1H, m), 2.15–2.22 (2H, m), 2.48–2.52 (1H, m), 2.70–2.79 (1H, m), 3.11 (1H, d, J 11.6 Hz), 3.20–3.28 (2H, m), 3.41 (1×, d, J 12.6 Hz), 4.36 (1H, d, J 11.6 Hz), 4.50 (1H, q, J 6.3 Hz), 7.15–7.31 (7H, m), 7.62 (1H, s).

MS (ES+) m/z 575 (M+2, 100%).

EXAMPLE 6

(3R)-1-((3R,4R,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid By analogy with Example 1 using the product from Description 39 to afford a crude oil. This was purified by preparative thin layer chromatography eluting with 7.5% methanol/dichloromethane to afford the title compound as a white foam.

$^1$H NMR (CDCl$_3$, 400 MHz): δ 1.08 (3H, s), 1.30 (3H, d, J 6.7 Hz), 1.30–1.32 (1H, m), 1.57–1.63 (2H, m), 1.64–1.74 (1H, m), 1.87 (1H, d, J 12.1 Hz), 1.91 (1H, d, J 11.7 Hz), 2.02 (1H, dd, J 12.5, 2.7 Hz), 2.09–2.16 (1H, m), 2.17–2.27 (1H, m), 2.31 (1H, t, J 10.2 Hz), 2.66 (1H, d, 11.7 Hz), 2.90–2.96 (1H, m), 3.20 (1H, t, J 10.2 Hz), 3.28 (1H, t, J 10.6 Hz), 3.52 (1H, td, J 10.2, 4.7 Hz), 4.14 (1H, dd, J 11.3, 3.9 Hz), 4.19–4.29 (2H, m), 6.95–7.00 (2H, m), 7.11–7.19 (5H, m), 7.64 (1H, s).

MS (ES+) m/z 574 (M+1, 100%).

EXAMPLE 7

[(3S,4R,5R)-5-{(1R)-1-[3,5-Bis(trifluoromethyl)phenyl]ethoxy}-4-phenyl-tetrahydropyran-3-yl]acetonitrile A mixture of product from Description 48 (3.62 g), potassium cyanide (0.97 g, 14.9 mmol), 18-crown-6 (1.5 g, 5.7 mmol) and dimethylsulphoxide (10 ml) was stirred at +60° C. over 6 hours, then treated with water (70 ml) and extracted into a 1:1 mixture of diethyl ether:i-hexane (3×). The combined organic extracts were washed with water, dried (Na$_2$SO$_4$) and concentrated in vacuo. The residue was purified by chromatography on silica to give the title compound (2.43 g, 83%).

$^1$H NMR (CDCl$_3$, 360 MHz): δ 1.30 (3H, d, J 6.7 Hz), 1.93 (1H, dd, J 17.2, 7.2 Hz), 2.10 (1H, dd, J 17.2, 3.5 Hz), 2.17 (1H, s), 2.56 (1H, dd, J 11.2, 10.2 Hz), 3.34 (1H, t, J 10.2 Hz), 3.38 (1H, t, J 10.2 Hz), 3.56 (1H, dt, J 9.8, 4.6 Hz), 4.10 (1H, dd, J 11.2, 4.2 Hz), 4.25 (1H, q, J 6.7 Hz), 4.27 (1H, dd, J 10.8, 4.9 Hz), 7.01 (2H, m) 7.18 (5H, m), 7.65 (1H, s).

EXAMPLES 8 AND 9

[(3S,4R,5R)-5-{(1R)-1-[3,5-Bis(trifluoromethyl)phenyl]ethoxy}-4-phenyl-tetrahydropyran-3-yl]methyl-2-methyl-2H-tetrazole; and

[(3S,4R,5R)-5-{(1R)-1-[3,5-bis(trifuoromethyl)phenyl]ethoxy}-4-phenyl-tetrahydropyran-3-yl]methyl-1-methyl-1H-tetrazole A mixture of the product from Description 49 (170 mg, 0.34 mmol), methyl iodide (0.2 ml), potassium carbonate (150 mg) and acetonitrile (1.5 ml) was stirred at +45° C. for 1 hour, and purified by PTLC chromatography on silica to give the N-2-methyl isomer (67 mg, 38%) and N-1-methyl isomer (77 mg, 41%).

EXAMPLE 8

[(3S,4R,5R)-5-{(1R)-1-[3,5-bis(trifluoromethyl) phenyl]ethoxy}-4-phenyl-tetrahydropyran-3-yl] methyl-2-methyl-2H-tetrazole $^1$H NMR (CDCl$_3$, 360 MHz): δ 1.30 (3H, d, J 6.3 Hz), 2.35–45 (3H, m), 2.64 (1H, m), 3.22 (1H, t, J 11.2 Hz), 3.29 (1H, t, J 10.9 Hz), 3.58 (1H, dt, J 9.8, 4.9 Hz), 3.96 (1H, dd, J 11.2, 3.9 Hz), 4.20 (1H, q, J 6.7 Hz), 4.22 (3H, s), 4.23 (1H, m), 7.07 (2H, m) 7.14 (3H, m), 7.19 (2H, s), 7.64 (1H, s).

EXAMPLE 9

[(3S,4R,5R)-5-{(1R)-1-[3,5-bis(trifluoromethyl) phenyl]ethoxy}-4-phenyl-tetrahydropyran-3-yl] methyl-2-methyl-2H-tetrazole $^1$H NMR (CDCl$_3$, 360 MHz): δ 1.30 (3H, d, J 6.3 Hz), 2.38 (1H, m), 2.47–2.57 (3H, m), 3.33 (1H, t, J 10.2 Hz), 3.40 (1H, t, J 10.9 Hz), 3.52 (3H, s), 3.56 (1H, dt, J 9.8, 4.9 Hz), 4.08 (1H, dd, J 11.2, 4.6 Hz), 4.24 (1H, q, J 6.3 Hz), 4.26 (1H, dd, J 11.6, 4.9 Hz), 7.01 (2H, m) 7.17 (5H, m), 7.64 (1H, s).

EXAMPLE 10

[(3S,4R,5R)-5-{(1R)-1-[3,5-bis(trifluoromethyl) phenyl]ethoxy}-4-phenyl-tetrahydro-pyran-3-yl] methyl-2,4-dihydro-1,2,4-triazol-3-one A mixture of the product from Description 50 (160 mg, 0.35 mmol), 1-[3-(dimethylamino)propyl]-3-ethylcarbodiimide hydrochloride (170 mg, 0.89 mmol), semicarbazide hydrochloride (97 mg, 0.87 mmol), N,N-dimethylaminopyridine (43 mg, 0.35 mmol) and dichloromethane (2 ml) was stirred at room temperature for 1 hour, then concentrated in vacuo. The residue was treated with 1M NaOH (8 ml) and the mixture was heated at reflux overnight. After cooling to room temperature, the mixture was quenched with 2M hydrochloric acid and extracted into dichloromethane. The combined organic extracts were dried (Na$_2$SO$_4$) and concentrated in vacuo. The residue was purified by PTLC chromatography on silica to give the title compound.

$^1$H NMR (CDCl$_3$, 360 MHz): δ 1.29 (3H, d, J 6.3 Hz), 2.08 (1H, dd, J 15.4, 9.5 Hz), 2.25 (1H, dd, J 15.4, 3.5 Hz), 2.32 (1H, m), 2.43 (1H, t, J 9.8 Hz), 3.20 (1H, t, J 10.9 Hz), 3.28 (1H, t, J 10.5 Hz), 3.54 (1H, dt, J 9.8, 4.9 Hz), 4.01 (1H, dd, J 11.2, 3.9 Hz), 4.19 (1H, q, J 6.3 Hz), 4.24 (1H, dd, J 10.9, 4.9 Hz), 7.03 (2H, m) 7.13 (3H, m), 7.17 (2H, s), 7.64 (1H, s), 9.05 (1H, s), 10.60 (1H, s).

EXAMPLE 11

3-((3S,4R,5R)-5-((1R)-1-(3,5-Bis(trifluoromethyl) phenyl)ethoxy)tetrahydro-4-phenylpyran-3-yl) methyl-1,2,4-triazole a) ((3S,4R,5R)-5-((1R)-1-(3,5-Bis(trifluoromethyl)phenyl) ethoxy)-4-phenyltetrahydropyran-3-yl)-((1-(2-trimethylsilyl)ethoxymethyl)-1,2,4-triazol-3-yl)methanol 1-(2-Trimethylsilyl)ethoxymethyl)-1,2,4-triazole (400 mg, 2 mmol) was dissolved in tetrahydrofuran (5 ml) and the solution was cooled to −78° C. n-Butyllithium (1.1 ml, 1.8 mmol) was added dropwise and the resulting solution was warmed to 10° C. then re-cooled to −78° C. A solution of the aldehyde of Description 46 (446 mg, 1 mmol) in tetrahydrofuran (3 ml) was added dropwise and the resulting yellow solution was allowed to warm to ambient temperature. The solution was quenched with citric acid (10 ml, 10% aqueous solution) and extracted with dichloromethane (3×10 ml). The organic extracts were dried (Na$_2$SO$_4$) and concentrated in vacuo. The yellow oil obtained was purified by chromatography on silica using 30–40% ethyl acetate in iso-hexane as eluant to give the title compound (a mixture of epimers at the carbinol centre) as a pale yellow oil (570 mg, 88%). Data for the major epimer are as follows:

$^1$H NMR (CDCl$_3$, 360 MHz): δ −0.01 (9H, s), 0.91 (2H, m) 1.36 (3H, d, J 6.5 Hz), 2.51 (1H, m), 2.99 (1H, d, J 5.5 Hz), 3.12 (1H, t, J 10.0 Hz), 3.37 (1H, t, J, 10-Hz), 3.46–3.56 (2H, m), 3.58–3.62 (1H, m), 3.82 (1H, dd, J 11.7, 4.4 Hz), 4.22–4.35 (2H, m), 4.45 (1H, 1H, m), 5.25 (1H, d, J 4.2 Hz), ), 7.18–7.421 (5H, m), 7.26 (2H, s), 7.68 (1H, s), 7.80 (1H, s).

b) Imidazole-1-carbothioc acid ((3S,4R,5R)-5-((1R)-1-(3,5-bis(trifluoromethyl)phenyl)ethoxy)-4-phenyltetrahydropyran-3-yl)-((1-(2-trimethylsilyl) ethoxymethyl)-1,2,4-triazol-3-yl)methyl ester The carbinol of a) above (570 mg, 0.88 mmol) and thiocarbonyldiimidazole (470 mg, 2.64 mmol) were dissolved in dichloroethane (3 ml) and the solution was heated under reflux for 12 hours. The mixture was concentrated in vacuo and the residue obtained was purified by chromatography on silica using 30–50% ethyl acetate in iso-hexane as eluant to give the title compound (as a mixture of epimers) as a pale yellow oil (500 mg, 75%). The mixture was used without further purification in the next step. Data for the major epimer are as follows:

$^1$H NMR (CDCl$_3$, 360 MHz): δ −0.03 (9H, s), 0.84 (2H, mc) 1.32 (3H, d, J 6.5 Hz), 2.52–2.60 (1H, m), 2.85 (1H, t, J 10.1 Hz), 3.35 (1H, t, J 10.1 Hz), 3.41–3.55 (2H, m), 3.61 1H, m), 3.71 (1H, t, J 10.1 Hz), 4.21 (1H, dd, J 11.7, 4.2 Hz) 4.23–4.34 (2H, m), 5.18 (2H, d, J 4.2 Hz), 5.99 (1H, d, J 2.4 Hz), 6.97–6.99 (2H, m), 7.09 (1H, s), 7.16–7.20 (5H, m), 7.60 (1H, s), 7.64 (1H, s), 7.78 (1H, s), 8.32 (1H, s). MS m/e 646 (100%, M$^+$−110).

c) 3-((3S,4R,5R)-5-((1R)-1-(3,5-Bis(trifluoromethyl) phenyl)ethoxy)-4-phenyltetrahydropyran-3-yl)methyl-1-(2-trimethylsilyl)ethoxymethyl-1,2,4-triazole The compound described in b) above (500 mg) and azobisisobutyronitrile (50 mg) were dissolved in toluene (10 ml) and added dropwise via syringe pump to a refluxing solution of tributyltin hydride (0.44 ml) in toluene (15 ml). The solution was cooled after 2 hours and was concentrated in vacuo and the residue obtained was purified by chromatography on silica using 10–50% ethyl acetate in iso-hexane as eluant to give the title compound as a pale yellow oil.

$^1$H NMR (CDCl$_3$, 360 MHz): δ −0.06 (9H, s), 0.98 (2H, t, J 7.7 Hz) 2.49–2.59 (4H, m), 3.37 (2H, t, J 10.5 Hz), 3.48 (2H, dt, J 9.2, 1.8 Hz), 3.56–3.66 (1H, m), 4.06 (1H, dd, J 10.0, 2.4 Hz), 4.26–4.36 (2H, m), 5.04 (1H, d, J 11.3 Hz), 5.09 (1H, d, J 11.3 Hz), 7.19–7.23 (3H, m), 7.25 (2H, s), 7.69 (1H, s), 7.79 (1H, s). MS m/e 630 (100%, M$^+$+1).

d) 3-((3S,4R,5R)-5-((1R)-1-(3,5-Bis(trifluoromethyl) phenyl)ethoxy)-4-phenyltetrahydropyran-3-yl)methyl-1,2, 4-triazole The compound described in c) above (500 mg) was dissolved in ethanol (20 ml) and HCl (5 ml, 5N) was added. The solution was heated under reflux for 3 hours. The solution was cooled and was concentrated in vacuo and the residue obtained was neutralised with solid Na$_2$CO$_3$. This mixture was dispersed between dichloromethane and water. The organic layer was dried ($Na_2SO_4$), concentrated in vacuo and purified by chromatography on silica using 2% dichloromethane in methanol as eluant to give the title compound as a white solid (230 mg).

$^1$H NMR ($CDCl_3$, 400 MHz): δ 1.29 (3H, t, J 6.5 Hz) 2.35–2.57 (4H, m), 3.25–3.31 (2H, m), 3.56 (1H, dt, J 9.8, 4.2 Hz), 4.00 (1H, dd, J 11.7, 3.4 Hz), 4.21 (2H, m), 7.03–7.06 (2H, m), 7.14–7.18 (3H, m), 7.18 (2H, s), 7.64 (1H, s), 7.93 (1H, s), 10.35 (1H, brs). MS m/e 500 (100%, M$^+$+1).

What is claimed is:

1. A compound of the formula (I):

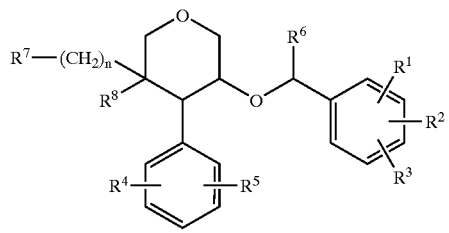

wherein:
- $R^1$ is hydrogen, halogen, $C_{1-6}$alkyl, $C_{1-6}$alkoxy, fluoro$C_{1-6}$ alkyl, fluoro$C_{1-6}$alkoxy, $C_{3-7}$cycloalkyl, $C_{3-7}$cycloalkyl$C_{1-4}$alkyl, $NO_2$, CN, SR$^a$, SOR$^a$, $SO_2R^a$, $CO_2R^a$, CONR$^a$R$^b$, $C_{2-6}$alkenyl, $C_{2-6}$alkynyl or $C_{1-4}$alkyl substituted by $C_{1-4}$alkoxy, wherein R$^a$ and R$^b$ each independently represent hydrogen or $C_{1-4}$alkyl;
- $R^2$ is hydrogen, halogen, $C_{1-6}$alkyl, fluoro$C_{1-6}$alkyl or $C_{1-6}$alkoxy substituted by $C_{1-4}$alkoxy;
- $R^3$ is hydrogen, halogen or fluoro$C_{1-6}$alkyl;
- $R^4$ is hydrogen, halogen, $C_{1-6}$alkyl, $C_{1-6}$alkoxy, fluoro$C_{1-6}$ alkyl, fluoro$C_{1-6}$alkoxy, hydroxy, $NO_2$, CN, SR$^a$, SOR$^a$, $SO_2R^a$, $CO_2R^a$, CONR$^a$R$^b$, $C_{2-6}$alkenyl, $C_{2-6}$alkynyl or $C_{1-4}$alkyl substituted by $C_{1-4}$alkoxy, wherein R$^a$ and R$^b$ are as previously defined;
- $R^5$ is hydrogen, halogen, $C_{1-6}$alkyl, fluoro$C_{1-6}$alkyl or $C_{1-6}$alkoxy substituted by $C_{1-4}$alkoxy;
- $R^6$ represents hydrogen or a $C_{1-4}$alkyl group optionally substituted by a hydroxy group;
- $R^7$ represents halogen, hydroxy, $C_{2-4}$alkenyl, $C_{2-4}$alkynyl, $C_{1-6}$alkoxy, $N_3$, —NR$^9$R$^{10}$, —NR$^a$COR$^b$, —OSO$_2$R$^a$, —(CH$_2$)$_p$NR$^a$(CH$_2$)$_q$COOR$^b$, COR$^a$, COOR$^a$, —N=C=O, a 5- or 6-membered cyclic ether which is optionally substituted at any substitutable position by one or two substituents selected from =O, =S, halogen, hydroxy, $C_{1-4}$alkyl, $C_{1-4}$alkoxy, fluoro$C_{1-4}$alkyl fluoro$C_{1-4}$alkoxy, COR$^e$ and CO$_2$R$^e$, or a five membered or six membered nitrogen-containing heteroaromatic ring optionally containing 1, 2 or 3 additional heteroatoms selected from N, O and S which heteroaromatic ring is optionally substituted at any substitutable position by a substituent selected from =O, =S, halogen, hydroxy, —SH, COR$^a$, CO$_2$R$^a$, -ZNR$^9$R$^{10}$, $C_{1-4}$alkyl, hydroxy$C_{1-4}$alkyl, fluoro$C_{1-4}$alkyl, chloro$C_{1-4}$alkyl, $C_{1-4}$alkoxy, fluoro$C_{1-4}$alkoxy or $C_{1-4}$alkoxy substituted by a $C_{1-4}$alkoxy or hydroxyl group, and wherein said $C_{2-4}$alkenyl and $C_{2-4}$alkynyl groups are optionally substituted by a substituent selected from halogen, hydroxy, $N_3$, —NR$^9$R$^{10}$, —NR$^a$COR$^b$, —OSO$_2$R$^a$, —(CH$_2$)$_p$NR$^a$(CH$_2$)$_q$COOR$^b$, COR$^a$ or COOR$^a$, and where R$^e$ is hydrogen, $C_{1-4}$alkyl or benzyl;

or R$^7$ represents a C-linked nitrogen-containing ring of the formula

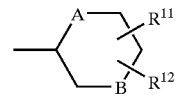

wherein A represents NR$^{13}$ or O, and

B represents a bond, CH$_2$, NR$^{13}$ or O, wherein one or both hydrogen atoms in said CH$_2$ moiety may be replaced with one or both of R$^{11}$ and R$^{12}$, or alternatively, one of the hydrogen atoms in said CH$_2$ moiety together with a hydrogen atom from an adjacent carbon are replaced by a double bond;

with the proviso that when A is O, then B is NR$^{13}$;

and with the further proviso that when R$^7$ represents said C-linked nitrogen-containing ring, n is zero and R$^8$ is hydrogen;

$R^8$ represents hydrogen, $C_{1-6}$alkyl, fluoro$C_{1-6}$alkyl, hydroxy, $C_{1-6}$alkoxy or hydroxy$C_{1-6}$alkyl;

$R^9$ is hydrogen, $C_{1-4}$alkyl, $C_{3-7}$cycloalkyl, $C_{3-7}$cycloalkyl$C_{1-4}$alkyl, $C_{2-4}$alkyl substituted by a $C_{1-4}$alkoxy or hydroxyl group, or $R^9$ is a five membered or six membered nitrogen-containing heteroaromatic ring as previously defined;

$R^{10}$ is hydrogen or $C_{1-4}$alkyl, $C_{3-7}$cycloalkyl, $C_{3-7}$cycloalkyl$C_{1-4}$alkyl, or $C_{2-4}$alkyl substituted by a $C_{1-4}$alkoxy or hydroxyl group;

or $R^9$, $R^{10}$ and the nitrogen atom to which they are attached form a heteroaliphatic ring of 4 to 7 ring atoms, optionally substituted by one or two groups selected from hydroxy, COR$^e$, CO$_2$R$^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group, or a five membered or six membered nitrogen-containing heteroaromatic ring as previously defined, or said heteroaliphatic ring is substituted by a spiro-fused lactone ring, and said heteroaliphatic ring optionally containing a double bond, which heteroaliphatic ring may optionally contain an oxygen or sulphur ring atom, a group S(O) or S(O)$_2$ or a second nitrogen atom which will be part of a NH or NR$^d$ moiety, where R$^d$ is $C_{1-4}$alkyl optionally substituted by hydroxy or $C_{1-4}$alkoxy;

or $R^9$, $R^{10}$ and the nitrogen atom to which they are attached form a non-aromatic azabicyclic ring system of 6 to 12 ring atoms;

or $R^9$, $R^{10}$ and the nitrogen atom to which they are attached form a heteroaliphatic ring of 4 to 7 ring atoms to which is fused a benzene ring or a five membered or six membered nitrogen-containing heteroaromatic ring optionally containing 1, 2 or 3 additional heteroatoms selected from N, O and S;

$R^{11}$ and $R^{12}$ each independently represent hydrogen, hydroxy, COR$^e$, CO$_2$R$^e$, $C_{1-4}$alkyl optionally substituted by a $C_{1-4}$alkoxy or hydroxyl group, or $C_{1-4}$alkoxy optionally substituted by a $C_{1-4}$alkoxy or hydroxyl group;

or, when they are attached to the same carbon atom, $R^{11}$ and $R^{12}$ may together represent =O, =CHCO$_2$R$^a$, —O(CH$_2$)$_m$O—, —CH$_2$O(CH$_2$)$_k$—, —CH$_2$OCH$_2$C(O)—, —CH$_2$OCH$_2$CH(OH)—, —CH$_2$OCH$_2$C(CH$_3$)$_2$—, —CH$_2$OC(CH$_3$)$_2$CH$_2$—, —C(CH$_3$)$_2$OCH$_2$CH$_2$—, —CH$_2$C(O)OCH$_2$—, —OC(O)

CH$_2$CH$_2$—, —C(O)OCH$_2$CH$_2$—, —C(O)OC(CH$_3$)$_2$CH$_2$—, —C(O)OCH$_2$C(CH$_3$)$_2$—, —OCH$_2$(CH$_2$)$_k$—, —OC(CH$_3$)$_2$CH$_2$CH$_2$—, —OCH$_2$C(CH$_3$)$_2$CH$_2$—, —OCH$_2$CH$_2$C(CH$_3$)$_2$—, —OCH$_2$CH=CHCH$_2$—, —OCH$_2$CH(OH)CH$_2$CH$_2$—, —OCH$_2$CH$_2$CH(OH)CH$_2$—, —OCH$_2$C(O)CH$_2$CH$_2$—, —OCH$_2$CH$_2$C(O)CH$_2$—, or a group of the formula

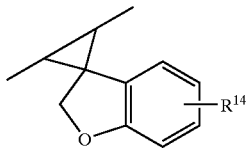

or, where they are attached to adjacent carbon atoms, R$^{11}$ and R$^{12}$ may together represent —OCH$_2$CH$_2$— or —OCH$_2$CH(OH)—, or R$^{11}$ and R$^{12}$ may together form a fused benzene ring;

or, R$^{11}$ and R$^{12}$ together form a C$_{1-2}$alkylene bridge across the pyrrolidine, piperidine, morpholine or piperazine ring to which they are attached;

R$^{13}$ represents hydrogen, benzyl, C$_{1-4}$alkyl, C$_{3-7}$cycloalkyl, C$_{3-7}$cycloalkylC$_{1-4}$alkyl, or C$_{2-4}$alkyl substituted by a C$_{1-4}$alkoxy or hydroxyl group;

R$^{14}$ represents hydrogen, halogen, hydroxy, C$_{1-4}$alkyl, hydroxyC$_{1-4}$alkyl or fluoroC$_{1-4}$alkyl;

Z represents a bond, C$_{1-6}$alkylene or C$_{3-6}$cycloalkylene;

k is 1, 2 or 3;

m is 1 or 2;

n is zero, 1 or 2;

p is 1 or 2; and q is 1 or 2;

or a pharmaceutically acceptable salt thereof.

2. The compound of claim 1 wherein R$^1$ is hydrogen, C$_{1-4}$alkyl, C$_{1-4}$alkoxy, halogen or CF$_3$.

3. The compound of claim 1 wherein R$^2$ is hydrogen, C$_{1-4}$alkyl, C$_{1-4}$alkoxy, halogen or CF$_3$.

4. The compound of claim 1 wherein R$^3$ is hydrogen, fluorine, chlorine or CF$_3$.

5. The compound of claim 1 wherein R$^4$ is hydrogen or fluorine.

6. The compound of claim 1 wherein R$^5$ is hydrogen, fluorine, chlorine or CF$_3$.

7. The compound of claim 1 wherein R$^6$ is C$_{1-4}$alkyl optionally substituted by hydroxy.

8. The compound of claim 1 wherein R$^7$ is NR$^{10}$R$^{11}$ where the group NR$^{10}$R$^{11}$ represents a heteroaliphatic rind of 4 to 7 ring atoms substituted by two groups, the first substituent being selected from hydroxy, CO$_2$R$^e$ (where R$^e$ is hydrogen, methyl, ethyl or benzyl), or C$_{1-2}$alkyl substituted by hydroxy, and the second substituent being a methyl group.

9. The compound of claim 1 wherein R$^8$ is hydrogen or methyl.

10. The compound of claim 1 wherein n is 1 or 2.

11. A compound of the formula (Ia);

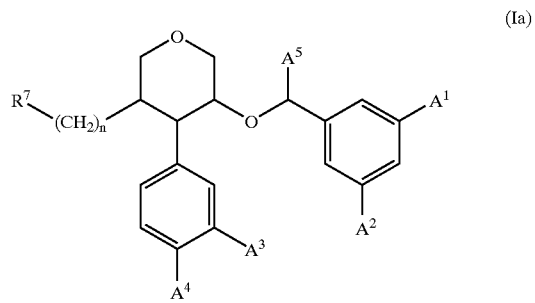

wherein:
A$^1$ is fluorine or CF$_3$;
A$^2$ is fluorine or CF$_3$;
A$^3$ is fluorine or hydrogen;
A$^4$ is fluorine or hydrogen;
A$^5$ is methyl;
R$^7$ is NR$^{10}$R$^{11}$ where the group NR$^{10}$R$^{11}$ represents a heteroaliphatic ring of 4 to 7 ring atoms substituted by two groups, the first substituent being selected from hydroxy, CO$_2$R$^e$ (where R$^e$ is hydrogen, methyl, ethyl or benzyl), or C$_{1-2}$alkyl substituted by hydroxy, and the second substituent being a methyl group; and
n is zero, 1 or 2;
or a pharmaceutically acceptable salt thereof.

12. A compound which is selected from the group consisting of:
(3R)-1-((3R,4S,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid;
(3R)-1-((3S,4S,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid;
(3R)-1-((3S,4R,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid;
(3R)-1-((3R,4R,5S)-5-{(1R)-1-[3,5-Bis(trifluoromethyl)phenyl]ethoxy}-tetrahydro-4-phenylpyran-3-ylmethyl)-3-methylpiperidine-3-carboxylic acid;
(3R)-1-((3R,4S,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid;
(3R)-1-((3S,4S,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid;
(3R)-1-((3R,4R,5R)-5-{(1R)-1-[3,5-Bis(trifluoromethyl)phenyl]ethoxy}-tetrahydro-4-phenylpyran-3-ylmethyl)-3-methylpiperidine-3-carboxylic acid;
[(3S,4R,5R)-5-{(1R)-1-[3,5-Bis(trifluoromethyl)phenyl]ethoxy}-4-phenyl-tetrahydropyran-3-yl]acetonitrile;
[(3S,4R,5R)-5-{(1R)-1-[3,5-Bis(trifluoromethyl)phenyl]ethoxy}-4-phenyl-tetrahydropyran-3-yl]methyl-2-methyl-2H-tetrazole;
[(3S,4R,5R)-5-{(1R)-1-[3,5-bis(trifluoromethyl)phenyl]ethoxy}-4-phenyl-tetrahydropyran-3-yl]methyl-1-methyl-1H-tetrazole;
[(3S,4R,5R)-5-{(1R)-1-[3,5-bis(trifluoromethyl)phenyl]ethoxy}-4-phenyl-tetrahydro-pyran-3-yl]methyl-2,4-dihydro-1,2,4-triazol-3-one;
3-((3S,4R,5R)-5-((1R)-1-(3,5-Bis(trifluoromethyl)phenyl)ethoxy)tetrahydro-4-phenylpyran-3-yl)methyl-1,2,4-triazole;

and pharmaceutically acceptable salts thereof.

13. A pharmaceutical composition comprising the compound of claim 1 and a pharmaceutically acceptable carrier or excipient.

14. A method for the treatment of pain or inflammation, migraine, emesis, postherpetic neuralgia, depression or anxiety, which method comprises administration to a patient in need thereof of a therapeutically effective amount of the compound of claim 1.

* * * * *